(12) United States Patent
Mohl et al.

(10) Patent No.: US 12,714,430 B2

(45) **Date of Patent: *Aug. 25, 2026**

(54) SYSTEM AND METHOD FOR TREATING HEART TISSUE

(71) Applicant: Miracor Medical SA, Awans (BE)

(72) Inventors: Werner Mohl, Altenmarkt-Thenneberg (AT); Gregor Neumayr, Upper Hutt (NZ); Alem Jusic, Vienna (AT)

(73) Assignee: Miracor Medical SA (BE)

( * ) Notice: Subject to any disclaimer, the term of this patent is extended or adjusted under 35 U.S.C. 154(b) by 491 days.

This patent is subject to a terminal disclaimer.

(21) Appl. No.: 17/977,656

(22) Filed: Oct. 31, 2022

(65) Prior Publication Data

US 2023/0047777 A1 Feb. 16, 2023

Related U.S. Application Data

(63) Continuation of application No. 17/169,925, filed on Feb. 8, 2021, now Pat. No. 11,517,318, which is a (Continued)

(51) Int. Cl.

*A61B 17/12* (2006.01)
*A61B 5/00* (2006.01)

(Continued)

(52) U.S. Cl.

CPC .... *A61B 17/12122* (2013.01); *A61B 5/02028* (2013.01); *A61B 5/33* (2021.01);

(Continued)

(58) Field of Classification Search

CPC .......... A61B 17/12122; A61B 17/1204; A61B 17/12136; A61B 5/318; A61M 25/010184; A61M 60/531; A61M 60/135

See application file for complete search history.

(56) References Cited

U.S. PATENT DOCUMENTS

| | | |
|---|---|---|
| 4,589,869 A | 5/1986 | Wernborg |
| 4,657,536 A | 4/1987 | Dorman |

(Continued)

FOREIGN PATENT DOCUMENTS

| | | |
|---|---|---|
| UA | 14911 U | 6/2006 |
| WO | WO 8910155 | 11/1989 |

OTHER PUBLICATIONS

'Cannulation' [online]. Medtronic, Inc. 2010 [retrieved May 27, 2010]. Retrieved from the Internet: <URL: http://www.medtronic.com/for-healthcare-professionals/products-therapies/cardiovascular/therapies/cannulation/index.htm>.

(Continued)

*Primary Examiner* — Alexander J Orkin

(74) *Attorney, Agent, or Firm* — Barnes & Thornburg LLP

(57) ABSTRACT

Some embodiments of a system or method for treating heart tissue can include a control system and catheter device operated in a manner to intermittently occlude a heart vessel for controlled periods of time that provide redistribution of blood flow. In particular embodiments, the system and methods may be configured to monitor at least one input signal detected at a coronary sinus and thereby execute a process for determining a satisfactory time period for the occlusion of the coronary sinus. In further embodiments, after the occlusion of the coronary sinus is released, the control system can be configured to select the duration of the release phase before the starting the next occlusion cycle.

19 Claims, 8 Drawing Sheets

Related U.S. Application Data continuation of application No. 16/281,837, filed on Feb. 21, 2019, now Pat. No. 10,912,570, which is a continuation of application No. 15/626,959, filed on Jun. 19, 2017, now Pat. No. 10,238,394, which is a continuation of application No. 15/246,976, filed on Aug. 25, 2016, now Pat. No. 9,681,875, which is a continuation of application No. 13/336,769, filed on Dec. 23, 2011, now Pat. No. 9,433,381, which is a continuation of application No. 13/335,564, filed on Dec. 22, 2011, now Pat. No. 8,177,704.

(51) Int. Cl.
*A61B 5/02* (2006.01)
*A61B 5/33* (2021.01)
*A61M 25/10* (2013.01)

(52) U.S. Cl.
CPC .......... *A61B 5/6859* (2013.01); *A61B 5/6869* (2013.01); *A61B 5/7239* (2013.01); *A61B 5/742* (2013.01); *A61B 17/1204* (2013.01); *A61B 17/12136* (2013.01); *A61M 25/1018* (2013.01); *A61M 25/10184* (2013.11)

(56) References Cited

U.S. PATENT DOCUMENTS

| | | | | |
|---|---|---|---|---|
| 4,671,796 | A | 6/1987 | Groshong et al. | |
| 4,701,166 | A | 10/1987 | Groshong et al. | |
| 4,705,501 | A | 11/1987 | Wigness et al. | |
| 4,887,608 | A | 12/1989 | Mohl et al. | |
| 4,934,996 | A | 6/1990 | Mohl et al. | |
| 4,943,277 | A | 7/1990 | Bolling | |
| 4,969,470 | A | 11/1990 | Mohl et al. | |
| 5,033,998 | A | 7/1991 | Corday et al. | |
| 5,156,600 | A | 10/1992 | Young | |
| 5,224,938 | A | 7/1993 | Fenton, Jr. | |
| 5,226,427 | A | 7/1993 | Buckberg et al. | |
| 5,466,216 | A | 11/1995 | Brown et al. | |
| 5,707,358 | A | 1/1998 | Wright | |
| 5,755,686 | A | 5/1998 | O'Neill et al. | |
| 5,779,685 | A | 7/1998 | Thompson et al. | |
| 6,500,145 | B1 | 12/2002 | Bicakci et al. | |
| 6,506,146 | B1 | 1/2003 | Mohl et al. | |
| 6,569,145 | B1 | 5/2003 | Shmulewitz et al. | |
| 7,331,922 | B2 | 2/2008 | Mohl et al. | |
| 7,717,855 | B2 * | 5/2010 | Caldarone .......... | A61B 5/02225 600/490 |
| 8,177,704 | B1 | 5/2012 | Mohl et al. | |
| 9,433,381 | B2 | 9/2016 | Mohl et al. | |
| 9,681,875 | B2 | 6/2017 | Mohl et al. | |
| 10,238,394 | B2 | 3/2019 | Mohl et al. | |
| 10,912,570 | B2 | 2/2021 | Mohl et al. | |
| 11,517,318 | B2 * | 12/2022 | Mohl ................. | A61B 5/02028 |
| 2002/0120232 | A1 | 8/2002 | Stumpp et al. | |
| 2008/0015404 | A1 | 1/2008 | Mohl et al. | |
| 2008/0119742 | A1 | 5/2008 | Mohl et al. | |
| 2010/0056849 | A1 | 3/2010 | Mohl et al. | |
| 2010/0130810 | A1 | 5/2010 | Mohl et al. | |
| 2011/0295302 | A1 | 12/2011 | Mohl et al. | |
| 2016/0361068 | A1 | 12/2016 | Mohl et al. | |

OTHER PUBLICATIONS

'Cardioplegia Delivery' [online]. Quest Medical, Inc. 2010 [retrieved May 27, 2010]. Retrieved from the Internet: <URL: http://www.questmedical.com/products/cardio_catheters.asp>.

'Global Myocardial Protection' [online]. Edwards Lifesciences, 2004 [retrieved May 27, 2010]. Retrieved from the Internet: <URL:http://ht.edwards.com/resourcegallery/products/cannulae/images/ar00519.pdf>.

'Letters to the Editor: A New Technique for Pulmonary Arterial Catheter Insertion into Coronary Sinus Using Transesophageal Echocardiography' [online]. International Anesthesia Research Society, 2003 [retrieved May 27, 2010]. Retrieved from the Internet: <URL: http://www.anesthesia-analgesia.org/content/97/1/298.full.pdf>.

'MiRCSP Cannulae' [online]. Medtronic, Inc. 2010 [retrieved May 27, 2010]. Retrieved from the Internet: <URL: http://www.medtronic.com/for-healthcare-professionals/products-therapies/cardiovascular/cannulae-products/mircsp-cannula/index.htm>.

'Myocardial Protection System' [online]. Quest Medical, Inc. 2010 [retrieved May 27, 2010]. Retrieved from the Internet: <URL: http://www.questmedical.com/products/mps.asp>.

'Performer CPB' [online]. Medtronic, Inc. 2007 [retrieved May 27, 2010]. Retrieved from the Internet: <URL: http://www.medtronic.com/cardsurgery/arrested_heart/downloads/200704933.pdf>.

'Retrograde Perfusion Cannulae' [online]. Medtronic, Inc. 2010 [retrieved May 27, 2010]. Retrieved from the Internet: <URL: http://www.medtronic.com/for-healthcare-professionals/products-therapies/cardiovascular/cannulae-products/retrograde-perfusion-cannulae/index.htm>.

Aigner et al. "Coronary Sinus Library, ICSO and PICSO" Society of Coronary Sinus Interventions, 2003. A. Holzhausens Nfg., Austria.

Alzubadidi et al., "Automatic Computation for Pressure Controlled Intermittent Coronary Sinus Occlusion." International Journal of Computer Science Issues, vol. 7, No. 6 (Nov. 2010), pp. 285-289.

Alzubaidi et al., "Electrocardiogram based Methodology for Computing of Coronary Sinus Pressure." International Journal of Computer Science Issues, vol. 8, No. 2 (May 2011), pp. 382-386.

Alzubaidi, L., "Accurate Methods of Calculating the Coronary Sinus Pressure Plateau." International Journal of Computer Science Issues, vol. 8, No. 1 (Jan. 2011), pp. 138-140.

Faxon et al., "Coronary Sinus Occlusion Pressure and Its Relation to Intracardiac Pressure." The American Journal of Cardiology, vol. 56 (Sep. 1985), pp. 457-460.

Hoffman et al. "Usefulness of Myocardial Blush Grade Early and Late After Primary Coronary Angioplasty for Acute Myocardial Infraction in Predicting Left Ventricular Function." The American Journal of Cardiology, vol. 92 (Nov. 2003), pp. 1015-1019.

Lazar, H., "Advantages of Pressure-Controlled Intermittent Coronary Sinus Occlusion Over Left Ventricle-Powered Coronary Sinus Retroperfusion." The Annals of Thoracic Surgery, vol. 71, No. 1 (2001), pp. 402.

Mina et al., "Pressure Controlled Intermittent Coronary Sinus Occlusion (PICSO) in Patients Undergoing Cardiac Resynchronization Therapy," Academic Paper, Biomedical Engineering, Austrian Research Centers, Wr. Neustadt, (2009), 1 pp.

Mohl et al., "Analysis of Left Ventricular Function After Emergency Coronary Artery Bypass Grafting for Life-Threatening Ischaemia Following Primary Revascularisation." European Journal of Cardio-thoracic Surgery, vol. 13 (1998), pp. 27-35.

Mohl et al., "Is activation of coronary venous cells the key to cardiac regeneration?" Macmillan Publishers Ltd., 2008. Nature Clinical Practice, Cardiovascular Medicine, vol. 5, No. 9, pp. 528-530.

Mohl et al., "Myocardial Protection via the Coronary Sinus Long-Term Effects of Intermittent Coronary Sinus Occlusion as an Adjunct to Reperfusion in Acute Myocardial Infarction." Circulation Journal, vol. 72 (Apr. 2008), pp. 526-533.

Mohl et al., "Reduction of Infarct Size Induced by Pressure-Controlled Intermittent Coronary Sinus Occlusion." The American Journal of Cardiology, vol. 53 (Mar. 1984), pp. 923-928.

Mohl et al., "The legacy of coronary sinus interventions: Endogenous cardioprotection and regeneration beyond stem cell research." The American Association for Thoracic Surgery, 2008. The Journal of Thoracic and Cardiovascular Surgery, vol. 136, No. 5, pp. 1131-1135.

Mohl, W., "Pressure Controlled Intermittent Coronary Sinus Occlusion—an Alternation to Retrograde Perfusion of Arterial Blood." Society of Coronary Sinus Interventions, (2002), pp. 2-7.

Mohl, W., "The Momentum of Coronary Sinus Interventions Clinically." Perspective, vol. 77, No. 1 (Jan. 1988), pp. 6-12.

(56) References Cited

OTHER PUBLICATIONS

Onorati et al., "Coronary Sinus Perfusion Reverses Ongoing Myocardial Damage in Acute Ischemia." Wiley Periodicals, Inc. 2009. Journal compilation, International Center for Artificial Organs and Transplantation and Wiley Periodicals, Inc., 33 (10), pp. 788-797.
Stone et al., "Impact of Normalized Myocardial Perfusion After Successful Angioplasty in Acute Myocardial Infarction." Journal of the American College of Cardiology, vol. 39, No. 4 (Feb. 2002), pp. 591-597.
Syeda et al., "The Salvage Potential of Coronary Sinus Interventions: Meta-Analysis and Pathophysiologic Consequences." The Journal of Thoracic and Cardiovascular Surgery, vol. 127, No. 6 (Jun. 2004), pp. 1703-1712.
Weigel et al., "Beck and back: A paradigm change in coronary sinus interventions—pulsatile stretch on intact coronary venous endothelium." The Journal of Thoracic and Cardiovascular Surgery, vol. 133, No. 6 (Jun. 2007), 13 pp.

* cited by examiner 120
110
112
129
122
121
131

132
134
137
135
133

122
129
129
129
129
129
129
L 120
126
123
124
125

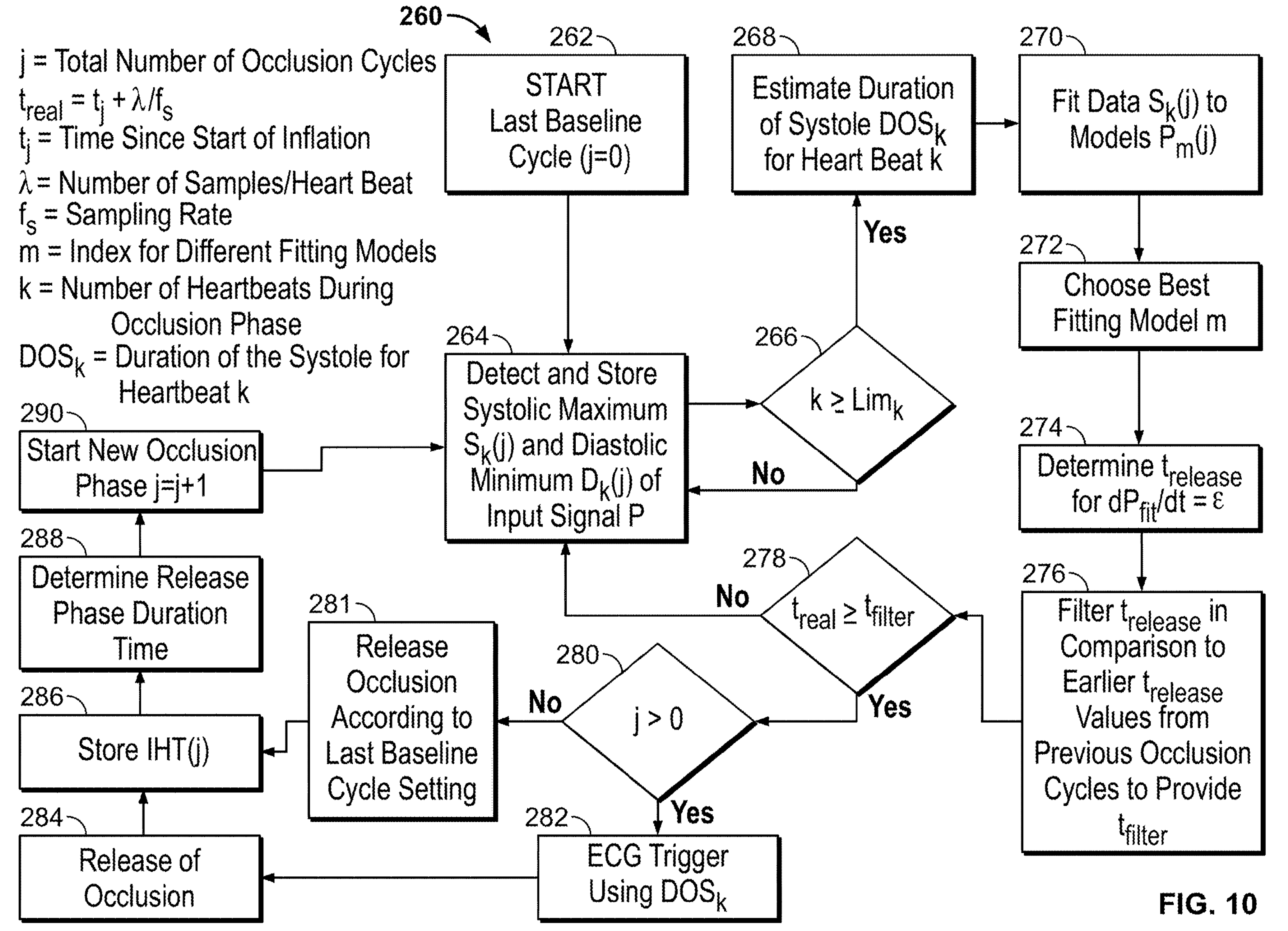
260
j = Total Number of Occlusion Cycles
t_real = t_j + λ/f_s
t_j = Time Since Start of Inflation
λ = Number of Samples/Heart Beat
f_s = Sampling Rate
m = Index for Different Fitting Models
k = Number of Heartbeats During Occlusion Phase
DOS_k = Duration of the Systole for Heartbeat k
262
START Last Baseline Cycle (j=0)
264
Detect and Store Systolic Maximum S_k(j) and Diastolic Minimum D_k(j) of Input Signal P
266
k ≥ Lim_k
Yes
No
268
Estimate Duration of Systole DOS_k for Heart Beat k
270
Fit Data S_k(j) to Models P_m(j)
272
Choose Best Fitting Model m
274
Determine t_release for dP_fit/dt = ε
276
Filter t_release in Comparison to Earlier t_release Values from Previous Occlusion Cycles to Provide t_filter
278
t_real ≥ t_filter
No
Yes
280
j > 0
No
Yes
281
Release Occlusion According to Last Baseline Cycle Setting
282
ECG Trigger Using DOS_k
284
Release of Occlusion
286
Store IHT(j)
288
Determine Release Phase Duration Time
290
Start New Occlusion Phase j=j+1
FIG. 10

SYSTEM AND METHOD FOR TREATING HEART TISSUE

CROSS-REFERENCE TO RELATED APPLICATION(S)

This is a continuation of U.S. application Ser. No. 17/169,925, filed on Feb. 8, 2021, and entitled "System And Method For Treating Heart Tissue," which is a continuation of U.S. application Ser. No. 16/281,837, filed on Feb. 21, 2019, and entitled "System and Method for Treating Heart Tissue," now issued as U.S. Pat. No. 10,912,570 on Feb. 9, 2021, which is a continuation of U.S. application Ser. No. 15/626,959, filed on Jun. 19, 2017, and entitled "System and Method for Treating Heart Tissue," now issued as U.S. Pat. No. 10,238,394 on Mar. 26, 2019, which is a continuation of U.S. application Ser. No. 15/246,976, filed on Aug. 25, 2016, and entitled "System and Method for Treating Heart Tissue," now issued as U.S. Pat. No. 9,681,875 on Jun. 20, 2017, which is a continuation of U.S. application Ser. No. 13/336,769, filed on Dec. 23, 2011, and entitled "System And Method For Treating Heart Tissue," now issued as U.S. Pat. No. 9,433,381 on Sep. 6, 2016, which is a continuation of U.S. application Ser. No. 13/335,564, filed on Dec. 22, 2011, and entitled "System And Method For Treating Heart Tissue," now issued as U.S. Pat. No. 8,177,704 on May 15, 2012, the contents of which are fully incorporated herein by reference.

TECHNICAL FIELD

This document relates to systems and methods that are configured to treat heart tissue, for example, by intermittently altering blood flow in a venous system to induce microcirculation within the heart tissue being treated.

BACKGROUND

The heart muscle receives arterial blood via coronary arteries so that the blood passes through and nourishes the heart muscle tissue. In some cases, a blockage in a coronary artery can result in a loss or reduction of blood flow through a portion of the heart muscle tissue, thereby creating an area of damaged or ischemic heart muscle tissue. The injury of the ischemic heart muscle tissue may also be exacerbated by reperfusion injury from a sudden reperfusion of blood to tissue that had been deprived of adequate blood flow. After the blockage is removed or otherwise opened to resume blood flow, the ischemic portion of the heart muscle tissue (such as the reperfused microcirculation) may be damaged to the point that normal blood flow does not return through the ischemic portion of the muscle tissue.

Some conventional systems attempt to repair or treat the ischemic heart muscle tissue by supplying the ischemic tissue with blood through retrograde perfusion. For example, the coronary sinus may be temporarily occluded so that the blood therein counterflows back from the coronary sinus through the coronary venous system and toward the ischemic muscle tissue that previously did not receive blood from the arterial side. The occlusion of the coronary sinus causes a pressure increase and, as a result, a redistribution of venous blood via the respective vein(s) into the capillaries of the border-zone ischemic muscle tissue so as to improve the supply of nutrients to that ischemic area. When the occlusion is ceased so that blood exits normally through the coronary sinus, the venous blood is flushed out while the metabolic waste products from the damaged tissue are carried off at the same time.

The combination of repeated venous pressure build-up phases followed by a phase of redistribution of flow and wash-out, often referred to as an intermittent coronary sinus occlusion ("ICSO") method, might in some circumstances improve arterial blood demand, improve microcirculation by reducing microvascular obstructions, provide a cardioprotective effect, and reduce ischemic tissue infarct size. When the timing of the ICSO method (e.g., the occlusion times and the release times) is controlled based upon monitored pressure measurements, the method is often referred to as pressure-controlled ICSO, or "PISCO." A computer-implemented control system may be used to control the timing of when to start and when to end, and hence the duration of, the occlusion phases that are performed during a PICSO method.

SUMMARY

Some embodiments of a system or method for treating heart tissue can include a control system and catheter device operated in a manner to intermittently occlude a heart vessel for controlled periods of time that provide effective and desirable redistribution of blood flow toward ischemic or otherwise damaged heart muscle tissue. In particular embodiments, the system and methods may be configured to monitor at least one input signal detected in the coronary sinus and thereby execute a process for determining a satisfactory time period for the occlusion of the coronary sinus. For example, the control system can be specifically programmed to monitor the input signals (e.g., the coronary sinus pressure in some embodiments) in real time during an occlusion phase of the coronary sinus and to calculate a release time (e.g., the time at which the occlusion should be released) in a manner that accounts for incidental outlier values from the input signal. Moreover, after the occlusion of the coronary sinus is released, the control system can be configured to calculate the duration of the release phase before the starting the next occlusion cycle.

Particular embodiments described herein may include a system for treating heart muscle tissue. The system may include a coronary sinus occlusion catheter including a distal tip portion comprising an adjustable occlusion device. The system may also include a control system to selectively activate the occlusion device for substantially occluding the coronary sinus during an occlusion phase. The control system may be configured to couple with a proximal portion of the coronary sinus occlusion catheter, and the control system may include a sensor signal input to receive a sensor data signal indicative of a hemodynamic performance parameter of a heart. Optionally, the control system may be configured to monitor the sensor data signal during the occlusion phase and to release the occlusion phase in response to a comparison of a first time value to a second time value, the second time value being determined at least in part from data points of the sensor data signal during the occlusion phase.

In other embodiments, a system for treating heart muscle tissue may include a coronary sinus occlusion catheter including a distal tip portion comprising an adjustable occlusion device. The system may also include a control system to selectively activate the occlusion device for substantially occluding the coronary sinus during an occlusion phase. The control system may be configured to couple with a proximal portion of the coronary sinus occlusion catheter, and the control system may include a sensor signal input to receive a sensor data signal indicative of a hemodynamic performance parameter of a heart. Optionally, the control system may be configured to determine a calculated release time in response to stored data points of the sensor data signal during the occlusion phase, and to determine a filtered release time value that is based at least partially upon the calculated release time and at least one previous release time value for at least one previous occlusion phase.

In some embodiments, a system for treating heart muscle tissue may include a coronary sinus occlusion catheter including a distal tip portion comprising an adjustable occlusion device. The system may also include a control system to selectively activate the occlusion device for substantially occluding the coronary sinus during an occlusion phase. The control system may be configured to couple with a proximal portion of the coronary sinus occlusion catheter, and the control system may include a sensor signal input to receive a sensor data signal indicative of a hemodynamic performance parameter of a heart. Optionally, the control system may be configured to detect and store a series of local maxima or minima of the sensor data signal during the occlusion phase, and may generate a curve fit function representing an envelope curve for the series of local maxima or minima. In such circumstances, the control system may determine a calculated release time for the occlusion phase based upon a time derivative of the curve fit function.

In further embodiments, a system for treating heart muscle tissue may include a coronary sinus occlusion catheter including a distal tip portion comprising an adjustable occlusion device. The system may also include a control system to selectively activate the occlusion device for substantially occluding the coronary sinus during an occlusion phase. The control system may be configured to deactivate the occlusion device for substantially non-occluding the coronary sinus during a release phase. Optionally, the control system may be configured to randomly select a duration time for the release phase from a predefined bracketed range of about 2 seconds to about 15 seconds.

In some alternative embodiments, a system for treating heart muscle tissue may include a coronary sinus occlusion catheter including a distal tip portion comprising an adjustable occlusion device. The system may also include a control system to selectively activate the occlusion device for substantially occluding the coronary sinus during an occlusion phase. The control system may be configured to deactivate the occlusion device for substantially non-occluding the coronary sinus during a release phase. Optionally, the control system may be configured to end the release phase after a release phase duration time that is from a predefined pattern of release phase duration times in a range about 2 seconds to about 15 seconds. The control system may store the predefined pattern of release phase duration times in a memory device.

In particular embodiments, a system for treating heart muscle tissue may include a coronary sinus occlusion catheter including a distal tip portion comprising an adjustable occlusion device. The system may also include a control system to couple with a proximal portion of the coronary sinus occlusion catheter. The control system may include a computer-readable memory storage device having computer-readable instructions stored thereon that, when executed by at least one processor, cause a number of operations to occur. For example, the computer-readable instructions may be executed by at least one processor to cause the control system to monitor a sensor data signal indicative of a hemodynamic performance parameter of a heart. Also, the computer-readable instructions may be executed by at least one processor to cause the control system to selectively activate the occlusion device for substantially occluding the coronary sinus during an occlusion phase. Further, the computer-readable instructions may be executed by at least one processor to cause the control system to deactivate the occlusion device for substantially non-occluding the coronary sinus during a release phase.

Some of the embodiments described herein may provide one or more of the following benefits. First, particular embodiments of the control system and catheter device can operate to intermittently occlude the coronary sinus or other heart vessel for controlled periods of time that provide effective redistribution of blood flow toward ischemic or otherwise damaged heart muscle tissue. The controlled periods of time may be accurately calculated by the control system based upon the input signals (for instance, the coronary sinus pressure) detected using the catheter device or another sensor device for use with the heart.

Second, some embodiments of the control system can be configured to execute an occlusion duration algorithm that is specifically adapted to calculate a satisfactory and effective time duration for the occlusion phase in a manner that accounts for (and reduces the implications of) outlier values of the input signal detected during the same occlusion phase. As such, the control system can execute the occlusion duration algorithm to reduce the likelihood that the occlusion phase with be released too early due to outlier values of the detected coronary sinus measured values (for instance, due to changes in coronary sinus pressure, coronary sinus velocity, volume flow or other measured parameters, e.g., caused by a patient's cough or other movement). Moreover, the control system can execute the occlusion duration algorithm to reduce the likelihood that the occlusion phase with be released too late due to one or more outlier values for the input signal. Thus, the occlusion duration algorithm may be employed by the control system to provide enhanced stability for the calculations of the intermittent occlusion time durations over a series of occlusion cycles.

Third, particular embodiments of the system can be used to provide a real-time response to the presently detected input signal (e.g., coronary sinus pressure signal in certain embodiments) during an occlusion phase so as to calculate the end of that same occlusion. Accordingly, each occlusion phase can be customized to the particular patient and to the particular condition occurring in the coronary sinus during that same occlusion phase.

Fourth, some embodiments of the system can be configured to trigger the release of the occlusion phase at a point within a heartbeat that provides an improved wash-out effect. For example, the control system can be configured to promptly deflate a balloon of the catheter device to release the occlusion of the coronary sinus at an approximate point in time of the next heart beat (e.g., triggered with the ECG signal of the heart or any other indicator of maximum wash out).

Fifth, in particular embodiments after the occlusion phase has been released, the control system can be configured to determine a suitable time period for the release phase. In some circumstances, the time period for the release phase can be restricted to predetermined range of time values regardless of the calculated time period for the occlusion phase and regardless of the input signals detected at the coronary sinus.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 10 is another process flow chart illustrating an algorithm for controlling the occlusion phase and release phase of the system of FIG. 1, in accordance with particular embodiments.

Like reference symbols in the various drawings indicate like elements.

DETAILED DESCRIPTION OF ILLUSTRATIVE EMBODIMENTS

Figure 1:
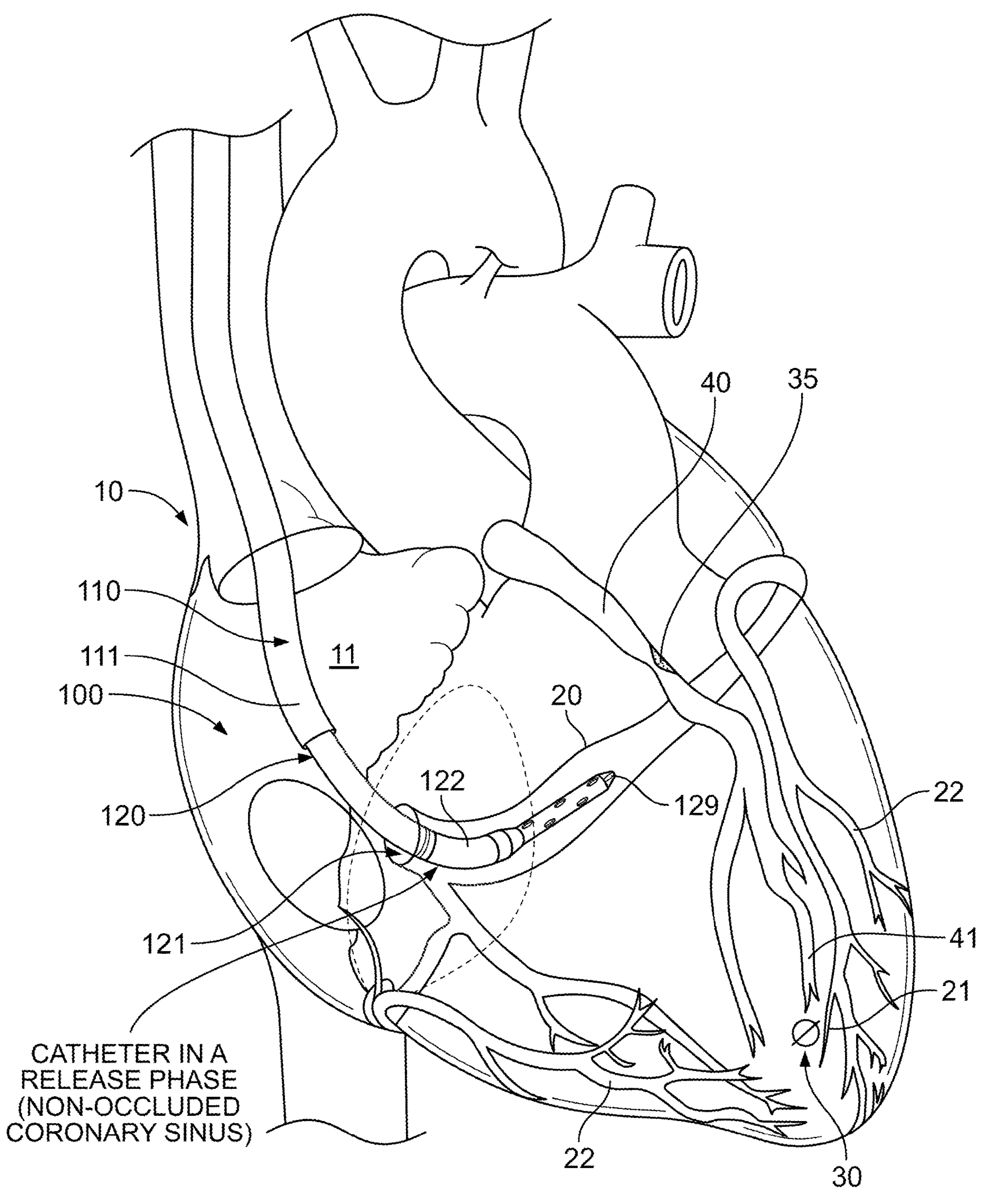
FIG. 1 is a perspective view of a portion of a system for treating heart tissue, including a catheter device in a non-occluding position, in accordance with some embodiments.
Figure 2:
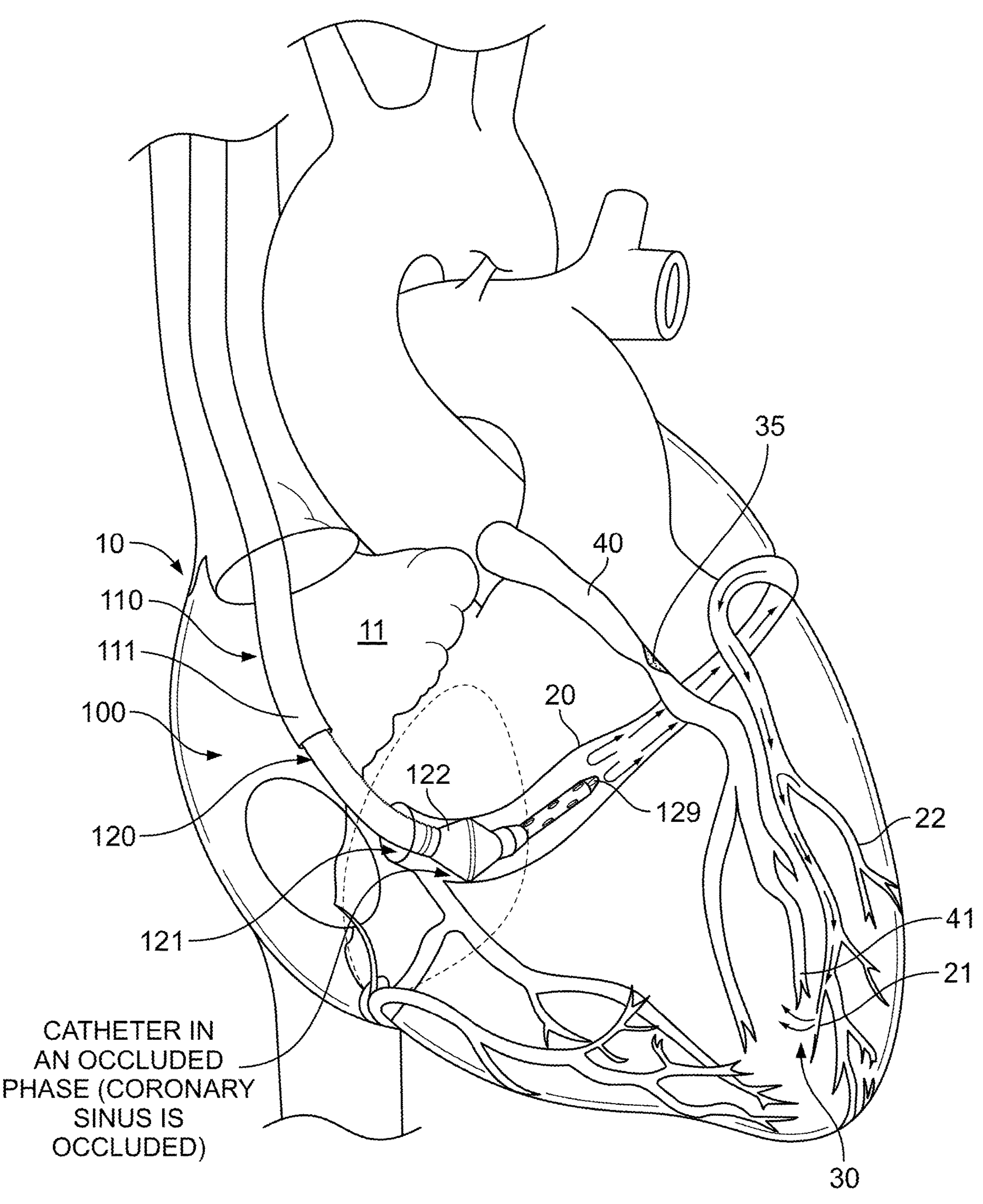
FIG. 2 is a perspective view of the portion of the system of FIG. 1, including the catheter device in an occluding position, in accordance with some embodiments.

Referring to FIGS. 1-2, some embodiments of a system 100 for treating heart tissue can include a coronary sinus occlusion catheter 120 configured to intermittently occlude a coronary sinus 20 of a heart 10. The catheter 120 can be configured to adjust between a non-occluding position (FIG. 1) and an occluding position (FIG. 2) so as to intermittently occlude the coronary sinus and thereby redistribute venous blood flow toward heart muscle tissue 30. In this embodiment, the coronary sinus occlusion catheter 120 includes a distal tip portion 121 and a proximal portion 131 (FIG. 6), which includes a proximal hub 132 configured to connect with an external control system 140 (FIG. 6) via a number of fluid or sensor lines. As described in more detail below, the control system 140 may be employed to operate one or more components at the distal tip portion 121 of the coronary sinus occlusion catheter 120 while also receiving one or more sensor signals that provide data indicative of a heart performance parameter (e.g., coronary sinus pressure, electrocardiogram (ECG) information, or another measured parameter indicative of hemodynamic performance of the heart). In some preferred embodiments, the control system 140 is configured to control the catheter 120 so as to occlude the coronary sinus in accordance with an specific algorithm (refer to FIG. 9 or 10).

Briefly, in use, the distal tip portion 121 of the coronary sinus occlusion catheter 120 can be arranged in a coronary sinus 20 of a heart 10 and thereafter activated to intermittently occlude the blood flow exiting from the coronary sinus 20 and into the right atrium 11. During such an occlusion of the coronary sinus 20, the venous blood flow that is normally exiting from the coronary sinus 20 may be redistributed into a portion of heart muscle tissue 30 that has been damaged due to blood deprivation or loss of functional myocardium. For example, the portion of heart muscle tissue 30 can suffer from a lack of blood flow due to a blockage 35 in a coronary artery 40. As a result, the arterial blood flow to the affected heart muscle tissue 30 via a local artery 41 can be substantially reduced such that the heart muscle tissue 30 becomes ischemic or otherwise damaged. Further, because the arterial blood flow is reduced, the venous blood flow exiting from the local vein 21 is likewise reduced. Other branch veins 22 located at different regions along the heart 10 may continue to receive blood flow, thereby creating a supply of venous blood flow exiting through the coronary sinus 20. In some embodiments, the coronary sinus occlusion catheter 120 can be delivered into the coronary sinus 20 and thereafter activated so as to intermittently occlude the coronary sinus 20 (refer to FIG. 2). Such an occlusion can cause the venous blood flow to be redistributed to the local vein 21 and then into the portion of heart muscle tissue 30 that suffers from a lack of blood flow due to the blockage 35 in the coronary artery 40. As such, the ischemic or otherwise damaged heart muscle tissue 30 can be treated with the redistributed venous blood flow so that the heart muscle tissue 30 receives an improved supply of nutrients. (As shown in FIGS. 1-2, the catheter 120 is deployed into the coronary sinus 20 before the arterial blockage 35 is repaired or removed to restore normal coronary arterial blood flow. However, in alternative embodiments, the arterial blockage 35 can be repaired or removed immediately before or contemporaneously during use of the catheter 120 to occlude the coronary sinus 20.)

Figures 3, 4, 5:
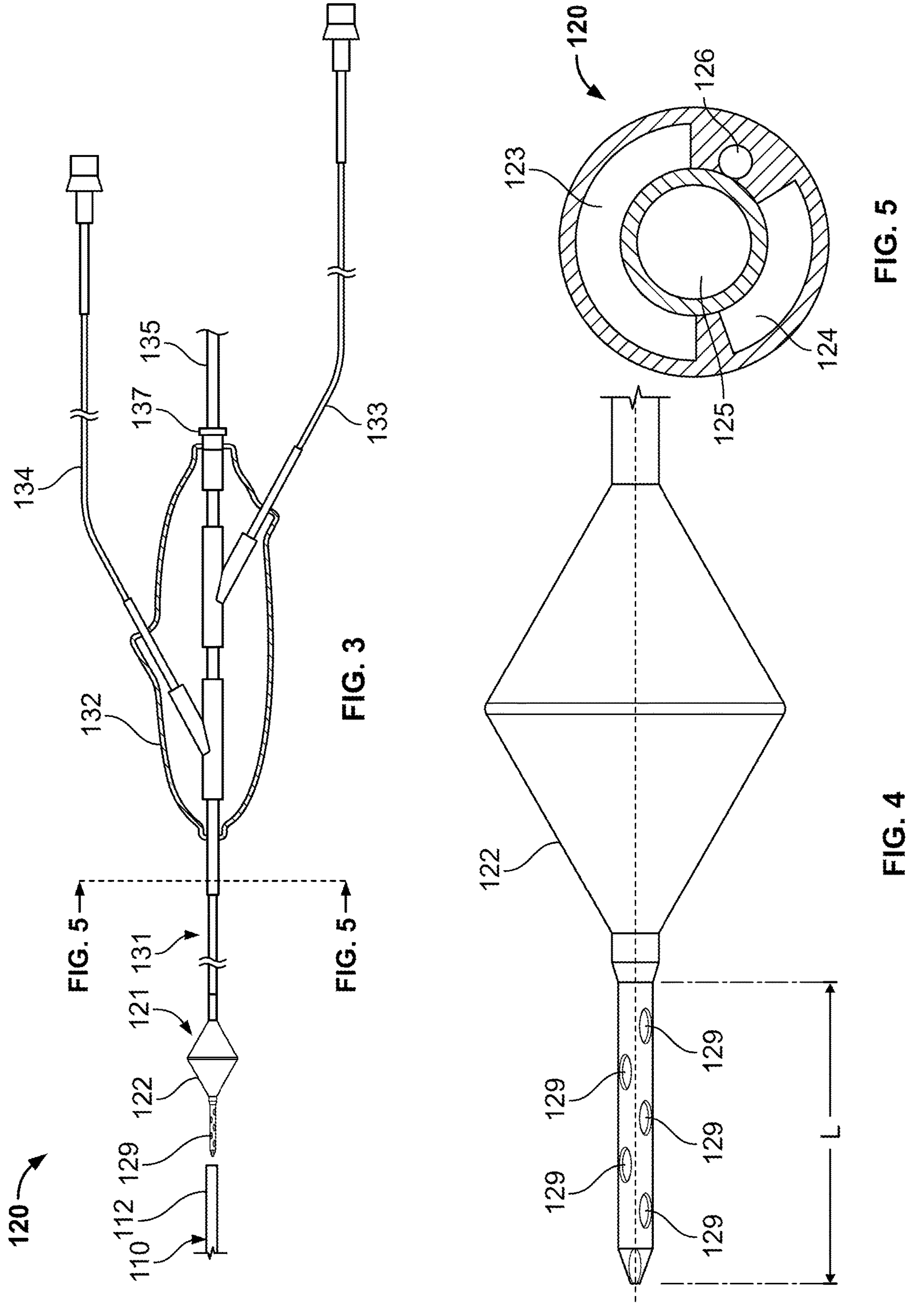
FIG. 3 is a cross-sectional view of a catheter device and a guide member of the system of FIG. 1.
FIG. 4 is a side view of a portion of the catheter device of FIG. 3.
FIG. 5 is a cross-sectional view of a shaft portion the catheter device of FIG. 3.

Still referring to FIGS. 1-2, the system 100 may include a guide member 110 that is advanced through the venous system of the patient and into the right atrium 11. The guide member 110 in this embodiment comprises a guide sheath having a lumen extending between a distal end 111 (FIG. 1) and a proximal end 112 (FIG. 4). In alternative embodiments, the guide member 110 can serve as a guidance for a guide wire having an exterior surface extending between the distal end and the proximal end. Optionally, the guide member 110 includes a steerable mechanism to control the orientation of the distal end so as to steer the distal end 111 through the venous system and into the right atrium 11. Also, the guide member 110 can include one or more marker bands along the distal end 111 so that the position of the distal end can be monitored during advancement using an imaging device.

After the guide member 110 is advanced into the right atrium 11, the distal end 111 may be temporarily positioned in the coronary sinus 20 or the coronary sinus ostium. From there, the distal tip portion 121 of the coronary sinus occlusion catheter 120 can be slidably advanced along the guide member 110 for positioning inside the coronary sinus 20. In the embodiments in which the guide member 110 comprises a guide sheath, the distal tip portion 121 of the coronary sinus occlusion catheter 120 can slidably engage with an interior surface of the lumen during advancement toward the coronary sinus 20. In the alternative embodiments in which the guide member 110 comprises a guide wire structure, the distal tip portion 121 of the coronary sinus occlusion catheter 120 can slidably advance over the exterior surface of the guide wire (e.g., a lumen 125 of the catheter 120 passes over the guide wire) during advancement toward the coronary sinus 20. After the coronary sinus occlusion catheter 120 reaches the coronary sinus 20, the distal end 111 of the guide member 110 can be withdrawn from the coronary sinus 20 and remain in the right atrium 11 for mechanical support during use of the coronary sinus occlusion catheter 120.

Figure 6:
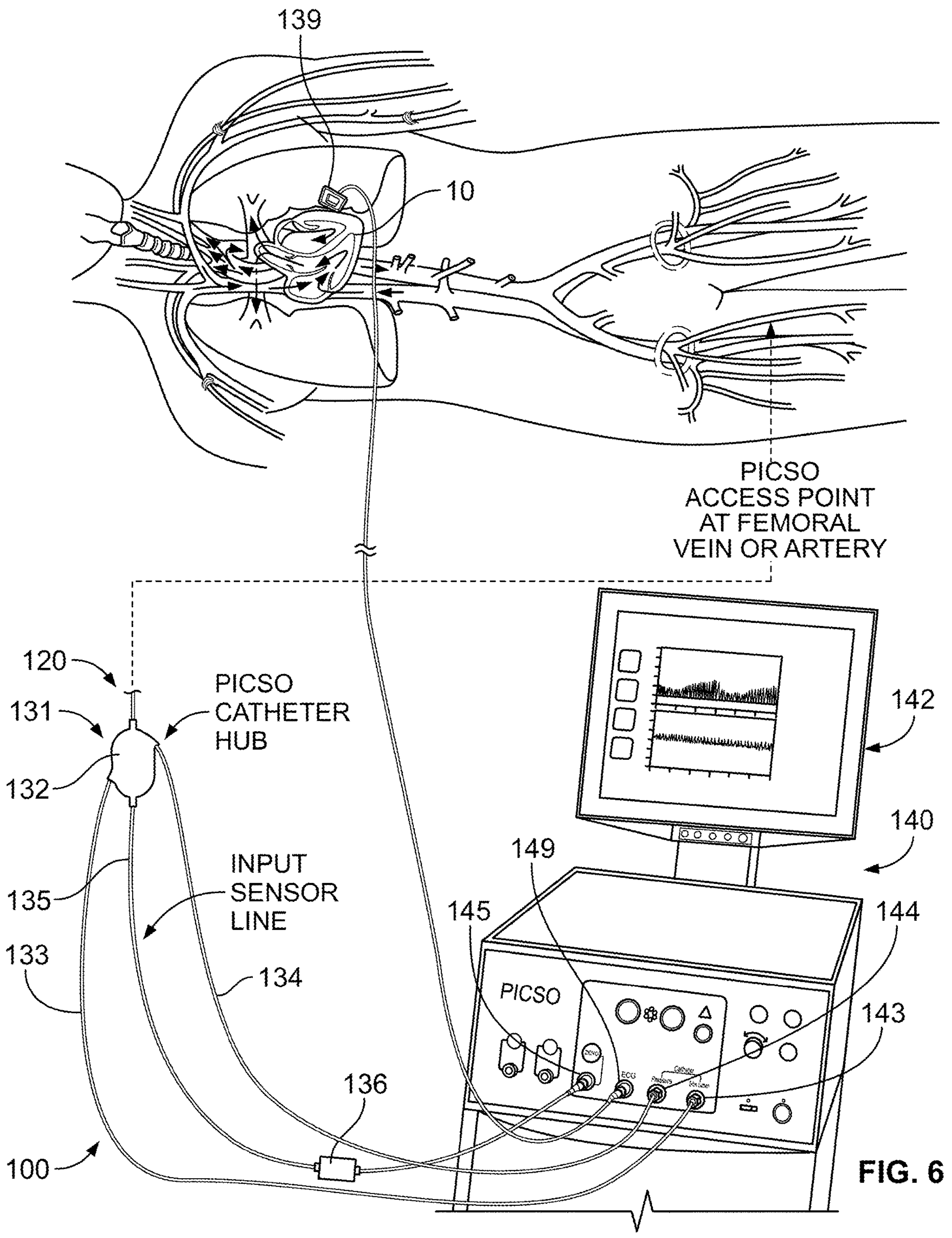
FIG. 6 is a perspective view of another portion of the system of FIG. 1.

Still referring to FIG. 1, the distal tip portion 121 of the coronary sinus occlusion catheter 120 that is positioned in the coronary sinus 20 includes an occlusion device 122, which in this embodiment is in the form of an inflatable balloon device. The occlusion device 122 can be activated so as to occlude the coronary sinus 20 and thereby cause redistribution of the venous blood into the heart muscle tissue 30 that is damaged due to a lack of arterial blood flow. As described in more detail below, the inflatable balloon device 122 can be in fluid communication with an internal lumen of the coronary sinus occlusion catheter 120, which is in turn in communication with a pneumatic subsystem of the control system 140 (FIG. 6). As such, the control system 140 can be employed to inflate or deflate the balloon device 122 in the coronary sinus.

The distal tip portion 121 also includes a one or more distal ports 129 that are positioned distally forward of a distal end of the occlusion device 122. In the depicted embodiments, the distal ports 129 as defined along a flexible elongate shaft portion that extends distally forward of a distal end of the occlusion device 122, and a majority or all of the distal ports face is a generally radially outward direction and are substantially uniformly spaced apart from one another along the circumference of the distal tip. As described in more detail below, the distal ports 129 may all be in fluid communication with a single sensor lumen (FIG. 5) extending through the coronary sinus occlusion catheter 120. Accordingly, at least one parameter of the coronary sinus (e.g., the coronary sinus pressure or other parameters indicative of hemodynamic performance as described below) can be monitored via a sensor device in communication with the distal ports 129.

Figure 7:
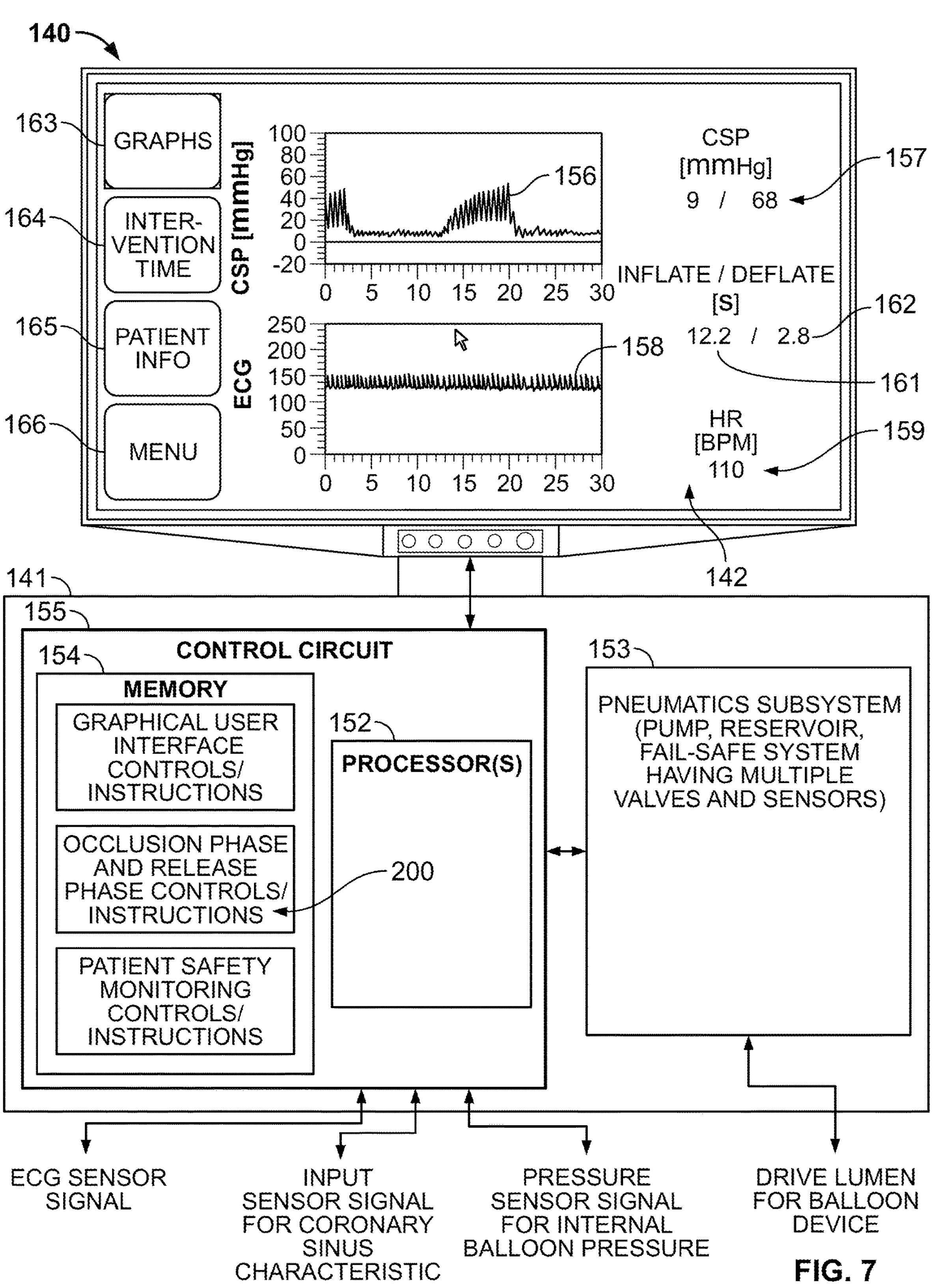
FIG. 7 is a diagram of a control system illustrated in the system of FIG. 6.

Referring now to FIGS. 3-5, the coronary sinus occlusion catheter 120 carries the occlusion device 122 along its distal tip portion 121 while the proximal hub 132 is arranged along the proximal portion 131. As previously described, the proximal hub 132 serves as the connection interface between a number of fluid or sensor lines 133, 134, and 135 (FIG. 3) and the corresponding lumens 123, 124, and 125 (FIG. 5) extending through the catheter 120. In this embodiment depicted in FIG. 3, the sensor line 135 is positioned as a central lumen 125 extending through the catheter 120. The sensor line 135 can be configured to communicate an input signal indicative of a measured parameter in the coronary sinus to the control system 140 (FIGS. 6-7). For example, the sensor line can be equipped with a sensor device (e.g., mounted near the distal ports 129) or otherwise equipped with a communication path between the distal ports 129 and the control system 140. As such, the catheter 120 can be configured to communicate at least one input signal indicative of a measured parameter in the coronary sinus, such as a fluid pressure (e.g., the coronary sinus pressure), a fluid temperature (e.g., using a temperature sensor positioned near the distal ports 129 and connected to the control system 140 via the sensor line 135), a volume or mass flow rate or rate of change thereof (e.g., using a flow sensor positioned near the distal ports 129 and connected to the control system 140 via the sensor line 135), an acceleration of the coronary sinus vessel (e.g., using one or more accelerometers positioned along the distal tip and connected to the control system 140 via the sensor line 135), a displacement of the coronary sinus vessel (e.g., using an ultrasound or optical measuring device to detect the movement of the coronary sinus vessel during each heartbeat), or another parameter indicative of hemodymanic performance of the heart (e.g., intra coronary sinus or other intra vessel electrocardiogram (ECG), contractility measurements, or the like).

In this particular embodiment, the sensor line 135 of the catheter 120 is configured to detect the coronary sinus pressure, which can be accomplished using a pressure sensor positioned near the distal ports 129 or using a fluid-filled path through the sensor line 135. For example, at least the sensor line 135 is connected to the proximal hub 132 using a Luer lock 137 so as to maintain the fluid path from the central lumen 125 of the catheter 120 to the lumen of the line 135.

As previously described, the system 100 may include the guide member 110 that is used to direct the coronary sinus occlusion catheter 120 through the venous system and into the heart 10. Referring to FIG. 3, the guide member 110 may be a guide sheath having a central lumen extending from a proximal end 112 (FIG. 4) to a distal end 111 (FIG. 1.) As previously described, the guide member 110 may be equipped with a steering mechanism (e.g., steel cables, a shape memory element, or the like) so that the practitioner can more readily advance the guide member 110 through the venous system and into the right atrium.

Still referring to FIGS. 3-5, the occlusion device 122 of the coronary sinus occlusion catheter 120 may comprise an inflatable balloon device having a predetermined shape when in the inflated condition. In this embodiment, the inflatable balloon device 122 includes a first conical portion narrowing down toward the distal direction, a second conical portion narrowing down toward the proximal direction, and a small generally cylindrical rim portion which is arranged between the conical portions. The narrowed ends of each of the conical portions are connected with the catheter shaft so as to provide a seal that prevents gas leakage from the balloon device 122. In the inflated condition, the diameter of the balloon device 122 in the region of the cylindrical rim portion is, for example, between about 12 mm and about 40 mm, and preferably about 35 mm. The longitudinal length of the balloon device is, for example, between about 20 mm and about 30 mm, and preferably about 25 mm. Optionally, the coronary sinus occlusion catheter 120 can be equipped with one or more marker bands positioned inside the balloon device 122 so as to be rendered visible during an interventional procedure by suitable imaging processes.

As shown in FIG. 5, the shaft of the coronary sinus occlusion catheter 120 extending distally from the proximal hub 132 can include a plurality of lumens 123, 124, 125, and 126. In this embodiment, the ring segment-shaped lumen 123 serves to supply and discharge fluid (e.g., helium gas in this embodiment) for inflating and evacuating the balloon device 122. The ring segment-shaped lumen 124, which is smaller than the other lumen 123, likewise communicates with the interior of the balloon device 122 and serves to measure the fluid pressure within the balloon device 122. The central lumen 125 in this embodiment is employed for measuring the coronary sinus pressure. The central lumen 125 is in fluid communication with the distal ports 129 of the catheter 125 so that the blood pressure in the coronary sinus is transferred to the fluid-filled path extending through the central lumen 125 and to the pressure sensor device 136 (FIG. 2). Alternatively, a miniature pressure sensor can be positioned immediate adjacent to the distal ports 129 such that a sensor wire (e.g., electrical or optical) extends through the central lumen 125 for communication with the control system 140 (FIG. 2). In this embodiment, the shaft of the coronary sinus occlusion catheter 120 includes a fourth lumen 126 having a circular cross section. One or more additional sensors or sensor wires can be positioned in this fourth lumen. Alternatively, a stiffening wire can be arranged in the fourth lumen 126 so as to extend through the catheter shaft in the region of the balloon device 122. The stiffening wire, which can comprise of a shape memory material such as Nitinol or can comprise piezo steering/stiffening elements, can be used to facilitate delivery of the distal tip portion 121 into the coronary sinus 20.

Referring to FIG. 4 in more detail, the distal ports 129 of the catheter 120 are arranged distally forward of the distal end of the balloon device 122 and are oriented to face generally radially outward from the end of the catheter 120. In the depicted embodiments, the distal ports 129 as defined along a flexible elongate shaft portion that extends distally forward of a distal end of the occlusion device 122, and optionally, the flexible elongate shaft portion that carries the distal ports 129 may extend for a longitudinal length that is greater than the longitudinal length of the balloon device 122. As such, the distal ports 129 of the coronary sinus occlusion catheter 120 can be configured so that the fluid pressure in the coronary sinus can be accurately measured even if a portion of the distal end abuts against the wall of the coronary sinus or any other vessel. In this embodiment, the distal ports 129 comprise three or more ports that are evenly spaced apart along the flexible elongate shaft portion and along a tapered tip, thereby enabling the fluid pressure in the coronary sinus to be applied into one or more of the ports 129 even if some of the ports 129 are positioned against a wall of the coronary sinus.

Referring now to FIGS. 6-7, the control system 140 can be configured to provide automated control of the occlusion device 122 of the coronary sinus occlusion catheter 120. As described in more detail below, the control system 140 includes a computer processor that executes computer-readable instructions stored on a computer memory device so as to activate or deactivate the occlusion in the coronary sinus 20 in accordance with a particular process (refer to FIG. 9 or 10). For instance, the control system 140 can be configured to release the occlusions phase (e.g., deflate the occlusion balloon 122 in this embodiment) in the coronary sinus 20 in response to a series of real-time measurements (e.g., coronary sinus pressure measurements in this embodiment) detected during the same occlusion phase. In addition, the control system 140 is equipped with a display device 142 having a graphical user interface that provides a practitioner or other users with time-sensitive, relevant data indicative of the progress of a coronary sinus occlusion procedure and the condition of the heart 10. As such, the user can readily monitor the patient's condition and the effects of intermittently occluding the coronary sinus 20 by viewing the graphical user interface while contemporaneously handling the coronary sinus occlusion catheter 120 and other heart treatment instruments (e.g., angioplasty catheters, stent delivery instruments, or the like).

As shown in FIG. 6, the proximal portion 131 of the coronary sinus occlusion catheter 120 and the control system 140 are positioned external to the patient while the distal tip portion 121 is advanced into the coronary sinus 20. The proximal portion 131 includes the proximal hub 132 that is coupled to the control system 140 via a set of fluid or sensor lines 133, 134, and 135. As such, the control system 140 can activate or deactivate the occlusion component 122 at the distal tip portion 121 of the coronary sinus occlusion catheter 120 while also receiving one or more sensor signals that provide data indicative of heart performance parameters (e.g., coronary sinus pressure, fluid temperature in the coronary sinus, volume or mass flow rate, rate of change of the volume or mass flow rate, acceleration of the coronary sinus vessel, displacement of the coronary sinus vessel, intra coronary sinus or other intra vessel electrocardiogram (ECG), surface electrocardiogram (ECG) information, contractility, or another measured parameter indicative of hemodynamic performance of the heart).

The proximal hub 132 of the coronary sinus occlusion catheter 120 serves to connect the plurality of fluid or sensor lines 133, 134, and 135 with the portion of the coronary sinus occlusion catheter 120 that extends into the patient's venous system. For example, the first line 133 extending between the control system 140 and the proximal hub 132 comprises a fluid line through which pressurized fluid (e.g., helium, another gas, or a stable liquid) can be delivered to activate the occlusion component (e.g., to inflate the inflatable balloon device 122). The fluid line 133 is connected to a corresponding port 143 of the control system 140 (e.g., the drive lumen port in this embodiment) so that the line 133 is in fluid communication with the pneumatic subsystem 153 housed in the control system 140 (as shown in FIG. 7). The proximal hub 132 joins the first line 133 with a balloon control lumen 123 (FIG. 5) extending through the coronary sinus occlusion catheter 120 and to the inflatable balloon device 122.

In another example, the second line 134 extending between the control system 140 and the proximal hub 132 comprises a balloon sensor line that is in fluid communication with the interior of the inflatable balloon device 122 so as to measure the fluid pressure within the balloon device 122. The proximal hub 132 joins the second line 134 with a balloon pressure lumen 122 (FIG. 5) extending through the coronary sinus occlusion catheter 120 and to the inflatable balloon device 122. The pressure of the balloon device 122 may be monitored by an internal control circuit 155 (FIG. 7) of the control system 140 as part of a safety feature that is employed to protect the coronary sinus 20 from an overly pressurized balloon device. The balloon sensor line 134 is connected to a corresponding port 144 of the control system 140 so that a pressure sensor arranged within the control system 140 can detect the fluid pressure in the balloon device 122. Alternatively, the pressure sensor may be arranged in the distal tip portion 121 or the in the proximal hub 132 such that only a sensor wire connects to the corresponding port 144 of the control system 140.

The proximal hub also connects with a third line 135 extending from the control system 140. As previously described, the third line can serve as the sensor line that is employed to communicate an input signal (as described above) to the control system 140. In this particular embodiment, the third line 135 comprises a coronary sinus pressure line that is used to measure the fluid pressure in the coronary sinus both when the balloon device 122 is inflated and when it is deflated. The proximal hub 132 joins the third line 135 with a coronary sinus pressure lumen 125 (FIGS. 4-5) extending through the coronary sinus occlusion catheter 120 and to the distal ports 129 that are forward of the balloon device 122. In this embodiment, the coronary sinus pressure lumen 125 and at least a portion of the third line 135 may operate as fluid-filled path (e.g., saline or another biocompatible liquid) that transfers the blood pressure in the coronary sinus 20 to pressure sensor device 136 along a proximal portion of the third line 135. The pressure sensor device 136 samples the pressure measurements (which are indicative of the coronary sinus pressure) and outputs an sensor signal indicative of the coronary sinus pressure to the corresponding port 145 of the controller system 140 for input to the internal control circuit 155 (FIG. 7). As described in more detail below, the coronary sinus pressure data are displayed by the graphical user interface 142 in a graph form 156 (refer to FIG. 7) so that a practitioner or other users can readily monitor the trend of the coronary sinus pressure while the coronary sinus 20 is in an occluded condition and in an non-occluded condition. Optionally, the graphical user interface 142 of the control system 140 can also output a numeric pressure measurement 157 (refer to FIG. 7) on the screen so that the practitioner can readily view a maximum coronary sinus pressure, a minimum coronary sinus pressure, the mean coronary sinus value, or all values. In alternative embodiments, the pressure sensor device 136 can be integrated into the housing of the control system 140 so that the third line 135 is a fluid-filled path leading up to the corresponding port 145, where the internal pressure sensor device (much like the device 136) samples the pressure measurements and outputs a signal indicative of the coronary sinus pressure.

Still referring to FIGS. 6-7, the system 100 may include one or more ECG sensors 139 to output ECG signals to the control system 140. In this embodiment, the system 100 includes a set of ECG sensor pads 139 (e.g., three sensor pads in some embodiments) that are adhered to the patient's skin proximate to the heart 10. The ECG sensors 139 are connected to the control system 140 via a cable that mates with a corresponding port 149 along the housing of the control system 140. As described in more detail below, the ECG data are displayed by the graphical user interface 142 in a graph form 158 (refer to FIG. 7) so that a practitioner or other user can readily monitor the patient's heart rate and other parameters while the coronary sinus is in an occluded condition and in an non-occluded condition. Optionally, the graphical user interface 142 of the control system 140 can also output numeric heart rate data 159 (refer to FIG. 7) (based on the ECG sensor data on the screen so that the practitioner can readily view the heart rate (e.g., in a unit of beats per minutes). The ECG sensor signals that are received by the control system 140 are also employed by the internal control circuit 155 (FIG. 7) so as to properly time the start of the occlusion period (e.g., the start time at which the balloon device 122 is inflated) and the start of the non-occlusion period (e.g., the start time at which the balloon device 122 is deflated). In addition, the control system may be equipped with additional ECG sensor signals capabilities to monitor the intra coronary, intra vessel or intra coronary sinus electrical ECG activity. These signals may be obtained from the coronary sinus occlusion catheter 120 measured at one or several locations alongside the shaft 139 or at the distal end where the distal ports 129 are located. Alternatively, or in addition, the ECG activity may be provided from another catheter in the heart such as the intra coronary ECG from an arterial vessel 40.

As shown in FIG. 7, some embodiments of the control system 140 include the internal control circuit subsystem 155 that communicates with the pneumatics subsystem 153. The control circuit subsystem 155 can include one or more processors 152 that are configured to execute various software modules stored on at least one memory device 154. The processors 152 may include, for example, microprocessors that are arranged on a motherboard so as to execute the control instructions of the control system 140. The memory device 154 may include, for example, a computer hard drive device having one or more discs, a RAM memory device, or the like that stored the various software modules.

In some embodiments, the memory device of the control circuit subsystem 155 stores a graphical user interface software module including computer-readable instructions for controlling the graphical user interface 142. These graphical user interface control instructions may be configured to cause the interface 142 (which includes a touch screen display device in this embodiment) to display: the pressure data graph 156 indicative of the coronary sinus pressure, the coronary sinus pressure numerical data 157, the ECG data graph 158, and the heart rate numerical data 159 (previously described in connection with FIG. 6). Optionally, the graphical user interface can be configured to display more than two the two graphs 157 and 158 on the screen. For example, in some embodiments, the graphical user interface can be configured to contemporaneously display three or four different graphs, such as the coronary sinus pressure numerical data 157, the ECG data graph 158, a third graph that depicts the arterial pressure as a function of time, and a fourth graph that illustrates another data output (e.g., the volume of blood flow).

Further, the graphical user interface control instructions stored in the control circuit subsystem 155 may be configured to cause the interface 142 to display numeric data of the time periods during which the coronary sinus is in an occluded state and in a non-occluded state. For example, the graphical user interface 142 can provide the occluded time numeric data 161 in units of seconds (e.g., 12.2 seconds as shown in FIG. 7). Also, the graphical user interface 142 can provide the non-occluded time numeric data 162 in units of seconds (e.g., 2.8 seconds as shown in FIG. 7). The graphical user interface control instructions stored in the control circuit subsystem 155 may be configured to cause the interface 142 to display a number of touch screen buttons 163, 164, 165, and 166 that enable the practitioner or other user to select different menu options or to input patient information or other data. In addition, the graphical user interface may be configured to utilize several of the data inputs to display unique determinants of the status of the procedure. This information may guide the user to understand when the heart is improving based on the therapy provided, and thus to understand when to terminate the therapy.

In addition, the graphical user interface control instructions stored in the control circuit subsystem 155 may be configured to cause the interface 142 to display a number of one or more alerts 167, which can be in the form of error messages or codes. The determination of which alert condition, if any, should be display is completed by the patient safety monitoring software module stored on the memory device 154, as described in more detail below.

Still referring to FIG. 7, the occlusion phase and release phase software module 200 stored on the memory device 154 can include computer-readable instructions that, when executed by one of the processors 152 (such as an embedded PC), causes the pneumatic subsystem 153 to activate or deactivate the balloon device 122 at selected times. As described in more detail below in connection with FIGS. 8-10, the control system 140 can be configured to execute the occlusion phase and release phase software module 200 stored on the memory device 154, which causes the control system to calculate the time periods during which the coronary sinus is in an occluded state and in a non-occluded state. In general, the software module 200 is designed to incorporate the expertise of a highly skilled cardiologist with years of experience in the calculation of when each occlusion phase should begin and when each occlusion phase should end in order to achieve a maximum clinical benefit of the desired mode of action, namely, altered venous side blood flow that induces microcirculation in a targeted heart tissue. The software module 200 may take into account various monitored parameters, and make the timing determinations in real-time, such that timing of each cycle of the method may be appropriate in light of monitored parameters.

This software module 200 can be configured to store sensor measurements during an occlusion phase, generate a curve fit of the sensor maxima or minima during that same occlusion phase, determine a time derivative of the curve fit line during that same occlusion phase, and use the time derivative of the curve fit line to calculate a time for releasing that occlusion phase. Moreover, as described in more detail below, the algorithm of the software module 200 may employ a weighted averaging function that takes previous release times into account when determining whether to release the present occlusion phase, thereby reducing the negative effects (e.g., premature or untimely release of the occlusion phase) that might otherwise result from outlier values input from the sensor line 135.

The patient safety monitoring software module stored on the memory device 154 can include computer-readable instructions that, when executed by one of the processors 152, causes the control circuit subsystem 155 to detect if any of the system sensors (e.g., the pressure sensors) output a measurement that is outside of a selected safety range. For example, if the coronary sinus pressure signal input to the control system 140 indicates a coronary sinus pressure that is above a selected threshold, the control circuit subsystem 155 can cause the graphical user interface 142 to display an alert in the form of a textual message or an error code. Further, in some embodiments, the control circuit subsystem 155 may automatically cause the pneumatic subsystem to deflate the balloon device 122 so as to immediately reduce the high pressure in the coronary sinus 20.

Still referring to FIG. 7, the pneumatic subsystem 153 of the control system 140 can be configured to promptly inflate or deflate the balloon device 122 in response to the control circuit subsystem. In some embodiments, the pneumatic subsystem may include a reservoir containing pressured gas, such as helium, and a vacuum pump. The reservoir and the vacuum pump can be controlled by a set of valves and are monitored by a set of pressure sensors that feedback into the control circuit subsystem 155. In such circumstances, the pneumatic subsystem can be configured to inflate or deflate the balloon device 122 at the distal tip portion 121 of the coronary sinus occlusion catheter 120 in less than 1 second, less that about 0.6 seconds, and preferably less than about 0.4 seconds.

Figure 8:
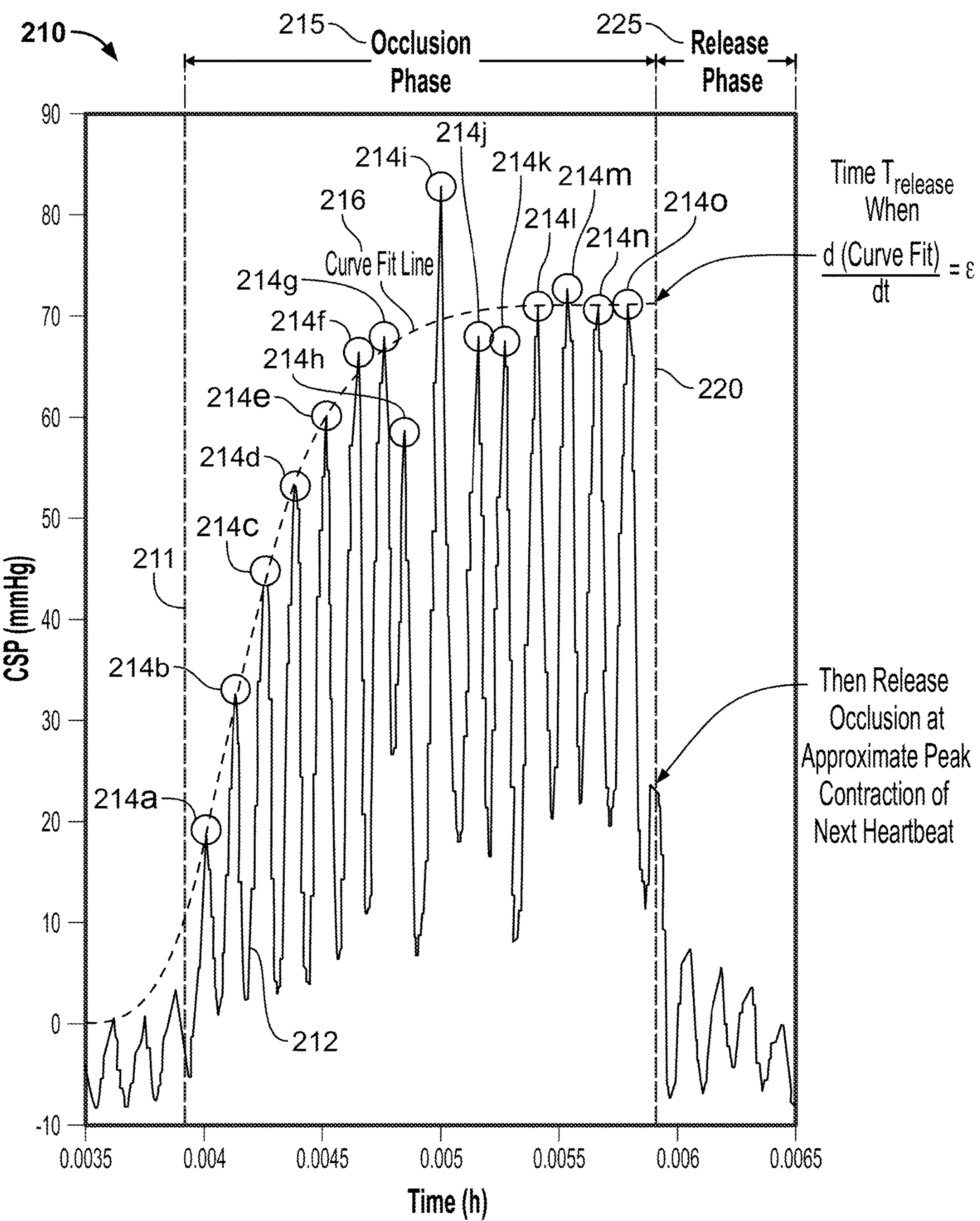
FIG. 8 is a diagram of a sensor signal input to a control system during an occlusion phase controlled by the control system of FIG. 7.

Referring now to FIG. 8, the occlusion phase and release phase software module 200 executed by the control system 140 can be configured to receive data from a sensor signal input 212 during an occlusion phase so as to calculate a desirable release time for releasing the occlusion phase. As shown in FIG. 8, a diagram 210 shows the data from the sensor signal input (e.g., a coronary sinus pressure sensor in this particular embodiment) that occurs over a series of heartbeats. This sensor data can be input to the control system 140 for purposes of executing an algorithm (refer, for example, to FIG. 9 or 10) at the control system 140 to determine when the occlusion device 122 of the catheter 120 should release the occlusion of the coronary sinus. In this embodiment, the sensor signal input represents the coronary sinus pressure sensor, but as previously described, the control system 140 can be configured to execute the calculation for determining the release of the occlusion phase based upon another signal that provides data indicative of heart performance parameters (e.g., coronary sinus pressure, fluid temperature in the coronary sinus, volume or mass flow rate, rate of change of the volume or mass flow rate, acceleration of the coronary sinus vessel, displacement of the coronary sinus vessel, intra coronary sinus or other intra vessel electrocardiogram (ECG), surface electrocardiogram (ECG) information, contractility, or another measured parameter indicative of hemodynamic performance of the heart). Optionally, the display device 142 (FIG. 7) of the control system 140 can be configured to display the diagram 210 of the sensor signal data that occurs over a series of heartbeats.

The control system 140 can be configured to monitor and store at least portions of the input from the sensor. For example, in the embodiment depicted in FIG. 8, the control system 140 is configured to detect and store the systolic maxima **214*a*-214*o* of the coronary sinus pressure signal 212 occurring over a series of consecutive heartbeats during the occlusion phase 215. (In other embodiments, the control system 140 may be configured to detect and store the local minima data points of the sensor input signal rather than local maxima data points of the sensor input signal.) Based upon these data points 214*a*-214*o*, the control system can be configured to perform a curve fitting operation so as to determine a "curve fit line" or "envelope" curve 216 for the pressure maxima occurring over a series of consecutive heartbeats during the occlusion phase 215. As described in more detail below in connection with each of FIGS. 9-10, the curve fitting operation can employ a "double exponential" function in particular embodiments, thereby providing a generally accurate representation of the trend of the systolic maxima data points 214*a*-214*o***.

Still referring to FIG. 8, the occlusion phase and release phase software module 200 executed by the control system 140 can be configured to calculate a preferred release time 220 of the occlusion phase 215 based upon a time derivative of the previously generated envelope curve 216. For example, the control system 140 can use the data points **214*a*-214*o* to generate the envelope curve 216 and thereafter accurately predict the time at which the time derivative of the envelope curve will equal a selected constant (ε, such as ε=0.05 in this embodiment). Thus, in this embodiment, the control system 140 can predict the time 220 at which the envelope curve 216 of the pressure maxima data points 214*a*-214*o* will approach a flatter slope. After the release time 220 is calculated, the occlusion phase and release phase software module 200 executed by the control system 140 may compare the actual time elapsed during the occlusion phase 215 to a weighted average of calculated release times including the most recent calculated release time 220 and previously calculated release times from previous occlusion phases. As described in connection with each of FIGS. 9 and 10, this comparison in the time domain may be performed to reduce the effect of outlier values of the sensor input signal (e.g., refer to the outlier value 214*h* or 214*i* as shown in FIG. 8), which might otherwise skew the calculation of the envelope curve 216 and thereby cause a premature or late release of the occlusion phase 215**.

When the actual time elapsed during the occlusion phase 215 is greater than or equal to the previously described weighted average of calculated release times, the control system 140 can be configured to release the occlusion phase 215 at a particular time point within a single heartbeat that can provide a significant washout effect (e.g., to enhance the removal of cellular waste products after the coronary sinus returns to a non-occluded state). For example, the control system 140 can monitor the ECG signal 149 (FIGS. 6-7) so as to trigger the release of the occlusion phase 215 at a time point approximately during a peak contraction of the heart (e.g., during a systolic pressure maximum).

Still referring to FIG. 8, the release phase 225 begins when the occlusion phase 215 is released. As described in more detail below, the occlusion phase and release phase software module 200 executed by the control system 140 can be configured to determine a time period for the release phase 225, after which the next occlusion phase would begin. For example, in some embodiments, the control system 140 can be configured to randomly select a time for ending the release phase 225 from a bracketed set of times that are empirically determined to provide a safe and effective release phase between occlusions phases (e.g., between about 3 seconds and about 6 seconds). In another example, the control system 140 can be configured to implement a time for ending the release phase 225 in accordance with a predetermined pattern of release phase time periods. In yet another example, the control system 140 can be configured to calculate a time for ending the release phase 225 based upon the data from the sensor signal input occurring during the release phase 225.

Figure 9:
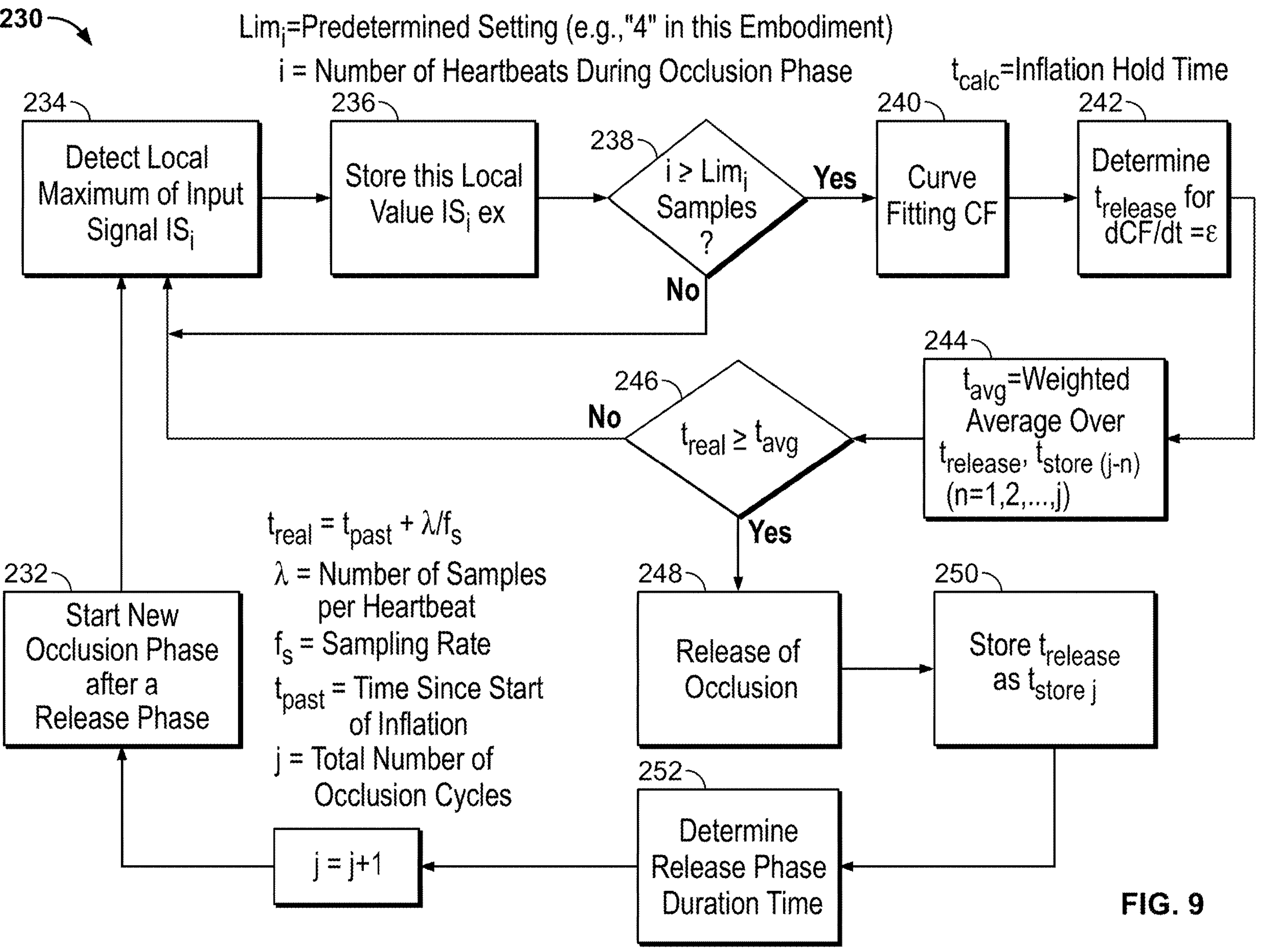
FIG. 9 is a process flow chart illustrating an algorithm for controlling the occlusion phase and release phase of the system of FIG. 1, in accordance with some embodiments.

Referring now to FIG. 9, some embodiments of the control system 140 can be configured to execute a process 230 for determining a release time for releasing an occlusion phase based at least in part upon data input from a sensor (e.g., the sensor signal input 212 described in connection with FIG. 8). For example, the occlusion phase and release phase software module 200 executed by the control system 140 can perform this process 230 to detect and store data points from the sensor signal, determine a curve fit (or "envelope" curve) for the data points, and then determine a release time based upon the envelope curved. This process 230 can be accomplished using a sensor input signal ($IS_i$) that provides data indicative of heart performance parameters (e.g., coronary sinus pressure, fluid temperature in the coronary sinus, volume or mass flow rate, rate of change of the volume or mass flow rate, acceleration of the coronary sinus vessel, displacement of the coronary sinus vessel, intra coronary sinus or other intra vessel electrocardiogram (ECG), surface electrocardiogram (ECG) information, contractility, or another measured parameter indicative of hemodynamic performance of the heart). In one example embodiment, this process 230 can use a sensor input signal ($IS_i$) indicative of the coronary sinus pressure (similar to that previously described in connection with FIGS. 6-8).

The process 230 can include an operation 232 in which a new occlusion phase is started. For example, the occlusion phase can be started after a release phase by activating the occlusion device 122 (FIGS. 1-2) of the catheter 120 to substantially occlude the coronary sinus 20. In some embodiments, the operation 232 in FIG. 9 can be illustrated by the start 211 of the occlusion phase 215 as shown in FIG. 8.

Still referring to FIG. 9, the process 230 can continue to operation 234 in which the control system 140 detects a local maximum of the sensor input signal ($IS_i$). For example, the local maximum of the sensor input signal ($IS_i$) may represent an individual pressure peak 214*a* (FIG. 8) of the coronary sinus pressure occurring during a heartbeat during the occlusions phase. The process 230 may also include the operation 236 of storing the local maximum value of the sensor input signal ($IS_i$). For example, this value can be stored in the computer memory of the control system 140. (It should be understood from the description herein, that in alternative embodiments of the process 230, the operations 234 and 236 may be implemented to detect and store the local minima data points of the sensor input signal or signals rather than local maxima data points of the sensor input signal.)

In operation 238, the process 230 determines if a selected number of samples for the local maxima have been detected and stored. For example, in this embodiment, the minimum number of sample data points (Lim') is 4 in this embodiment. Thus, the first heartbeat (i=1) after the start of the occlusion would provide a first data point, the second heartbeat (i=2) after the start of the occlusion would provide a second data point, and so forth. If the number of data points for the local maxima is less than the predefined setting (e.g., less than 4 in this embodiment), the process 230 returns to the operations 234 and 236 for another iteration to detect and store another data point. An example of this is illustrated in the first three data points 214*a-c* shown in FIG. 8.

After the minimum number of sample data points have been collected and stored (e.g., four data points after four heartbeats in this embodiment), the process 230 then continues to the next operation 240 in which the data points are employed to calculate a curve fit function (or an "envelope" curve). The curve fit model can be selected based upon the type of input signal (e.g., a coronary sinus pressure measurement or another type of sensor measurement) and a number of other factors. In this embodiment, the process 230 executed by the control system 140 can use a "double exponential" model to determine the curve fit function that represents an envelope of the local maxima data points previously detected and stored during the occlusion phase. For example, when the data points represent the values for the local maxima of coronary sinus pressure, the double exponential model can be:

$$CurveFit(t) = Ae^{B(1-e^{-Ct})-1},$$

where t=the time elapsed since the start of the occlusion phase, and

A, B, and C are curve fitting parameters

As previously described, the double exponential model can be used to determine the proper envelope curve of the data points to thereby provide a generally accurate representation of the trend of the systolic maxima data points occurring during the occlusion phase.

Still referring to FIG. 9, the process may also include an operation 242 in which the release time ($t_{release}$) is calculated based upon a time derivative of the curve fit function that was previously determined in earlier operation 240. For example, the control system 140 can use the data points of the local maxima to generate the curve fit function (or the "envelope" curve) and thereafter accurately predict the time at which the time derivative of the envelope curve (dCF/dt) will equal a predefined constant ε(e.g., ε=0.05 in this embodiment). In such circumstances, the envelope curve (dCF/dt) may be equal to or less than the predefined constant ε when the envelope curve of the local maxima data points approaches a flatter slope. Thus, by solving for the release time ($t_{release}$) when the time derivative of the envelope curve (dCF/dt) equals a predefined constant ε(0.05 in this embodiment), the process 230 is predicting the time during the occlusion phase at which the local maxima will trend toward an asymptotic value.

As shown in FIG. 9, the process 230 may not necessarily release the occlusion at the calculated release time ($t_{release}$). Rather, in operation 244, the calculated release time ($t_{release}$)

is used together with previously calculated release times from earlier occlusion cycles to generate a weighted average release time ($t_{avg}$). For the weighted average model create an average value that is weighted in favor of the most recent calculated release time ($t_{release}$) and the more recent release times from previous occlusion cycles. For example, in some embodiments, the model used by the process 230 to generate the weighted average release time ($t_{avg}$) may be:

$$t_{avg}(j) = \frac{\sum_{i=0}^{j} e^{-i} t_{release}(j-i)}{\sum_{i=0}^{j} e^{-i}},$$

where j=the total number of occlusion phases, $t_{release}$(j)=most recently calculated release time ($t_{release}$), and $t_{release}$(1, 2, . . . )=previously calculated release times from earlier occlusion cycles (1, 2, . . . )

It should be understood from the description herein that other weighted average models can be employed by the process 230 as an alternative to the aforementioned example.

In operation 246, the actual time elapsed during the occlusion phase ($t_{real}$) is compared to the weighted average release time ($t_{avg}$). This comparison in the time domain may be performed to reduce the effect of outlier values of the sensor input signal (e.g., refer to the outlier value 214*h* or 214*i* as shown in FIG. 8), which might otherwise skew the determination of the envelope curve and thereby cause a premature or late release of the occlusion phase 215. If the actual time elapsed during the occlusion phase ($t_{real}$) is less than the weighted average release time ($t_{avg}$), the occlusion phase should not yet be released, and the process 230 returns to the operation 234 for another iteration that employs another local maximum data point.

In operation 248, the occlusion phase is released when the actual time elapsed during the occlusion phase ($t_{real}$) is greater than or equal to the weighted average release time ($t_{avg}$). For example, the occlusion phase and release phase software module 200 executed by the control system 140 can indicate that the control system 140 should adjust the occlusion device 122 (FIG. 2) to no longer occlude the coronary sinus. In response, the pneumatics subsystem 153 (FIG. 7) may evacuate or otherwise actuate the occlusion device 122 (FIG. 2). In some embodiments, the control system 140 can be configured to release the occlusion phase at a particular time point within a single heartbeat that can provide a significant washout effect (e.g., to enhance the removal of cellular waste products after the coronary sinus returns to a non-occluded state). For example, the control system 140 may monitor the ECG signal 149 (FIGS. 6-7) or any other ECG signal so that the occlusion device 122 is shifted to the non-occluded position (FIG. 1) at a time point approximately during a peak contraction (or systolic pressure maximum) of the heart (refer to FIG. 8).

After the occlusion phase is released, operation 250 is performed by the process 230 to store the most recent calculated release time ($t_{release}$) in the computer memory (stored as $t_{store\ j}$) for subsequent use in a later calculation of the weighted average release time ($t_{avg}$) during a subsequent occlusion phase.

The process 230 may also include operation 252 in which the control system determines the duration time for the release phase. In this embodiment, the occlusion phase and release phase software module 200 executed by the control system 140 can be configured to determine the time duration for the release phase by a module that randomly selects a duration time from a bracketed set of times that are empirically determined to provide a safe and effective release phase between occlusions phases (e.g., between about 2 second and about 15 seconds, between about 2 seconds and about 6 seconds, and preferably between about 3 seconds and about 6 seconds). For example, the control system 140 randomly implement a duration time of 3.3 seconds for a first release phase, a duration time of 4.2 seconds for a second release phase, a duration time of 3.9 seconds for a third release phase, yet another randomly selected duration time (e.g., selected from the bracketed range between 3 seconds and 6 seconds) for a fourth release phase, and so forth.

In an alternative embodiment, the operation 252 can be accomplished by the control system 140 implementing a duration time for the release phase in accordance with a predetermined pattern of release phase time periods. In one example, the control system 140 can be configured to implement a duration time of 3.0 seconds for a first release phase, a duration time of 3.5 seconds for a second release phase, a duration time of 4.5 seconds for a third release phase, a duration time of 5.0 seconds for a fourth release phase, a duration time of 5.5 second for a fifth release phase, and then return to the start of the pattern for a duration time of 3.0 second for a sixth release phase.

In yet another alternative embodiment, the operation 252 can be accomplished by the control system 140 calculating a time for ending the release phase 225 based upon the data from the sensor signal input occurring during the release phase 225. For example, the control system 140 can be configured to detect and store the local maxima (or minima) of the sensor input signal occurring over a series of heartbeats during the release phase, calculate a curve fit function based upon the local maxima (or minima) data points, and thereafter calculate a duration time for the release phase based at least in part upon the curve fit function calculated from the local maxima (or minima) data points detected during the release phase.

Finally, after duration time for the release phase is reached, the process 230 may return to operation 232 in which a new occlusion phase is started. This cyclical process can continue for an extended period of minutes or hours, thereby resulting in numerous cycles of occlusion phases and release phases. Accordingly, in some embodiments, the coronary sinus occlusion catheter 120 (FIGS. 1-2) may continue to intermittently occlude the coronary sinus (FIGS. 1-2) to thereby redistribute the venous blood flow to the damaged portion of the heart muscle tissue 30. The duration of time for using the coronary sinus occlusion catheter 120 to intermittently occlude the coronary sinus 20 may be determined by a practitioner based upon a number of factors, including the trend of the input sensor signals (e.g., the trend of coronary sinus pressure measurements as displayed on the user interface 142 of FIG. 7 or a derivate thereof), a measurement of particular bio-markers present in the patient's blood (e.g., lactate (which increases in the event of ischemia), potassium (an indicator of ischemic tissue), and the like), or a combination thereof or another input signal.

Referring now to FIG. 10, some embodiments of the control system 140 can be configured to execute a process 260 for determining a release time for releasing an occlusion phase based at least in part upon data input from a sensor (e.g., the sensor signal input 212 described in connection with FIG. 8). In this embodiment, the process 260 can optionally accommodate one or more "baseline" occlusion cycles during an initial treatment after the catheter 120 is delivered, in which a predetermined pattern of intermittent coronary sinus occlusion time periods are implemented before the occlusion time periods become dependent upon the sensor signal input. Also, in this embodiment, the process can employ more than one curve fit model to the data points, and thereafter select which of the curve models best fits the data points. As described in more detail below, such operations can provide improved accuracy and flexibility in modeling the sensor input data.

In some embodiments, the process 260 may optionally include operation 262 in which the last "baseline" occlusion cycle is started. For example, during an initial phase when the catheter 120 is first delivered into the coronary sinus 20 and initially activated, the control system 140 can inflate and deflate the balloon device 122 according to the predetermined pattern of occlusion duration times and release duration times. This predetermined pattern of occlusion and release phases can be used to provide a "baseline" of sensor signal data points. During these time periods in the initial baseline phase, data points from sensor signal input may be recorded by the control system 140 (and displayed on the user interface 142), but the time periods for the occluded state and the non-occluded state are predetermined and do not change based upon the data points from the sensor signal input. As shown in FIG. 10, during operation 262 the cycle index "j" is set to "0" so that when the process 260 continues throughout other steps, the process 260 will eventually follow the path of operations 280 and 281 to thereby release the occlusion in accordance with the last predetermined baseline cycle. After the end of the final baseline cycle, the process 260 may continue for numerous additional cycles in which at least the duration times for occlusion phase are dependent upon the data gathered from the sensor signal input. (After the final baseline cycle or if the process 260 is implemented without any baseline cycle, the cycle index "j" starts at "1" so that when the process 260 continues throughout other steps, the process 260 will eventually follow the path of operations 282 and 284 to release the occlusion phase at a duration time based at least in part upon the data from the sensor input signal.)

Still referring to FIG. 10, the process may also include operation 264 in which systolic maximum and diastolic minimum (e.g., the local maximum and local minimum occurring at a heartbeat k) of the sensor input signal (P) are detected and stored by control system 140. For example, the systolic maximum of the sensor input signal (P) may represent an individual pressure peak 214*a* (FIG. 8) of the coronary sinus pressure occurring during a heartbeat (k) during the occlusions phase, and the diastolic minimum of the sensor input signal (P) may represent an individual pressure valley of the coronary sinus pressure occurring immediately before or after the systolic maximum. These values may be stored, for example, in the computer memory of the control system 140.

In operation 266, the process 260 determines if a selected number of samples for the systolic maxima and diastolic minima have been detected and stored. For example, in this embodiment, the minimum number of sample data points ($Lim_k$) is 4 in this embodiment. Thus, the first heartbeat (k=1) after the start of the occlusion would provide a first data point for each of the systolic maximum and diastolic minimum, the second heartbeat (k=2) after the start of the occlusion would provide a second data point for each of the systolic maximum and diastolic minimum, and so forth. If the number of data points for each of the systolic maxima and diastolic minima is less than the predefined setting (e.g., less than 4 in this embodiment), the process 260 returns to the operation 264 for another iteration to detect and store another data point for each of the systolic maximum and diastolic minimum.

After the minimum number of sample data points have been collected and stored (e.g., after four heartbeats in this embodiment), the process 260 then continues to the next operation 268, in which the duration of the systole ($DOS_k$) for the most recent heart beat (k) is estimated. For example, the duration of the systole ($DOS_k$) can be calculated as the time difference between a recently detected and stored diastolic minimum and the systolic maximum. As described in more detail below, the value for duration of the systole ($DOS_k$) can be stored for use in a subsequent operation (operation 282 in FIG. 10).

Still referring to FIG. 10, the process 260 may also include the operation 270 in which the data points (e.g., the systolic maxima data points in this embodiment) are used with one or more curve fitting models to generate one or more curve fit functions. Each of the curve fit functions may represent an "envelope" curve that indicates a trend for the systolic maxima data points stored during the operation 264. The multiple different curve fit models used in operation 270 can be selected based upon the type of input signal (e.g., a coronary sinus pressure measurement or another type of sensor measurement) and a number of other factors (such as parameters describing the status of the current heart physiology). In this embodiment, the operation 270 can use at least a "double exponential" model to determine the curve fit function that represents an envelope of the local maxima data points detected and stored during this occlusion phase. For example, when the data points represent the values for the local maxima of coronary sinus pressure, the double exponential model can be:

$$CurveFit_1(t) = Ae^{B\left(1-e^{-Ct}\right)-1},$$

where t=the time elapsed since the start of the occlusion phase, and

A, B, and C are curve fitting parameters

In addition, other curve fit models can be employed to generate a different curve fit function. For example, the additional curve fit model can use a "mono exponential" model, stretched exponential functions, or multi exponential functions. In one example of a "mono exponential function can be:

$$CurveFit_2(t) = A\left(1-e^{-Bt}\right),$$

where t=the time elapsed since the start of the occlusion phase, and

A and B are curve fitting parameters

After the one or more curve fit functions are determined by operation 270, the process can continue to operation 272 in which one the best of the curve fit functions is selected. In particular, the operation 272 may be performed to determine which of the multiple curve fit functions provides the best fit or most accurate representation of the trend of the systolic maxima data points occurring during the occlusion phase.

Still referring to FIG. 10, after one of the curve fit functions is selected in operation 272, the process 260 may also include an operation 274 in which the release time ($t_{release}$) is calculate based upon a time derivative of the particular curve fit function that was selected in earlier operation 270. As previously described, the control system 140 can use the curve fit function (or the "envelope" curve) to thereby accurately predict the time at which the time derivative of the envelope curve (dCF/dt) will equal a predefined constant ε(e.g., ε=0.05 in this embodiment). In such circumstances, the envelope curve (dCF/dt) may be equal to or less than the predefined constant ε when the envelope curve of the local maxima data points approach a generally flat slope. Thus, by solving for the release time ($t_{release}$) when the time derivative of the envelope curve (dCF/dt) equals a predefined constant ε(0.05 in this embodiment), the process 260 is predicting the time during the occlusion phase at which the local maxima will trend toward a generally consistent value.

In operation 276, the calculated release time ($t_{release}$) can be filtered so as to reduce the effect of outlier values of the sensor input signal (e.g., refer to the outlier value 214*h* or 214*i* as shown in FIG. 8). In this embodiment, the operation 276 can be used to filter the calculated release time ($t_{release}$) in comparison to previously calculated release times from earlier occlusion cycles, the result of which can generate a filtered release time ($t_{filtered}$). In one example, the filtered release time ($t_{filtered}$) can be calculated using weighted average of the calculated release time ($t_{release}$) and the previously calculated release times from earlier occlusion cycles. For example, in some embodiments, the model used by the filtering operation 276 to generate the filtered release time ($t_{filtered}$) may be:

$$t_{filter}(j) = \frac{\sum_{i=0}^{j} e^{-i} t_{release}(j-i)}{\sum_{i=0}^{j} e^{-i}},$$

where j=the total number of occlusion phases, $t_{release}$(j)=most recently calculated release time ($t_{release}$), and $t_{release}$(1, 2, . . . )=previously calculated release times from earlier occlusion cycles (1, 2, . . . )

It should be understood from the description herein that other filtering models can be employed by the operation 276 as an alternative to the aforementioned example.

In operation 278, the actual time elapsed during the occlusion phase ($t_{real}$) is compared to the weighted average release time ($t_{filter}$). As previously described, this comparison in the time domain may be performed to reduce the effect of outlier values of the sensor input signal (e.g., refer to the outlier value 214*h* or 214*i* as shown in FIG. 8), which might otherwise skew the determination of the envelope curve and thereby cause a premature or late release of the occlusion phase. If the actual time elapsed during the occlusion phase ($t_{real}$) than the weighted average release time ($t_{filter}$), the occlusion phase should not yet be released, and the process 260 returns to the operation 264 for another iteration that employs another local maximum data point.

As shown in FIG. 10, if the actual time elapsed during the occlusion phase ($t_{real}$) is greater than or equal to the weighted average release time ($t_{filter}$), the process 260 then determines if the control system 140 is performed the final baseline cycle or is instead performing a sensor-dependent cycle. As previously described, during the earlier operation 262 the cycle index "j" is set to "0" so that when the process 260 reaches operation 280, the process 260 will continued to operation 281 to thereby release the occlusion in accordance with the last predetermined baseline cycle (e.g., a predetermined duration time for the occlusion cycle that is not dependent upon the data from the sensor input signal). Alternative, during one of the numerous additional cycles after the baseline cycle, the duration times for occlusion phase are dependent upon the data gathered from the sensor signal input (and the cycle index "j" starts at "1" and increments upward with each additional cycle). In these circumstances, when the process 260 reaches operation 280, the process 260 will continue to operations 282 and 284 (described below) to release the occlusion phase at a duration time based at least in part upon the data from the sensor input signal.

In operation 282, the control system can employ an ECG-trigger so as to release the occlusion phase at a particular time point within a single heartbeat that can provide a significant washout effect. In particular, the control system 140 may monitor the ECG signal 149 (FIGS. 6-7) or any other ECG signal so that the occlusion device 122 is shifted to the non-occluded position (FIG. 1) at a time point approximately during a peak contraction (or systolic pressure maximum) of the heart (refer to FIG. 8). The particular point in time may be predicted using the duration of the systole ($DOS_k$) for the most recent heart beat (k) (as previously stored during operation 268). In some circumstances, the particular point in time within the single heartbeat may be predicted in a manner that accounts for the system-inherent time delay (e.g., an "ECG-trigger delay") based on the mechanical properties of the catheter, the pneumatic circuit of console and catheter, the electro-mechanical behavior of the controls of the pneumatic circuitry, e.g. valves, the software delays in the control units of the console. The ECG-trigger delay can be established empirically based on the overall system behavior of console and catheter. The ECG-trigger delay can be employed to as part of the release-time determination so that the release of occlusion can occur at a peak systolic pressure within a heartbeat, which may provide an improved washout effect from the coronary sinus.

In operation 284, the occlusion phase is released at the predicted point in time approximately during a peak contraction of the heart (as determined in operation 282). For example, the occlusion phase and release phase software module 200 executed by the control system 140 can indicate that the control system 140 should adjust the occlusion device 122 (FIG. 2) to no longer occlude the coronary sinus. In response, the pneumatics subsystem 153 (FIG. 7) may evacuate or otherwise actuate the occlusion device 122 (FIG. 2).

After the occlusion phase is released, operation 286 is performed by the process 260 to store the most recent calculated release time ($t_{release}$) in the computer memory (stored as $t_{store\ j}$) for subsequent use in a later calculation of the filtered release time ($t_{filter}$) during a subsequent occlusion phase.

The process 260 may also include operation 288 in which the control system determines the duration time for the release phase. In this embodiment, the occlusion phase and release phase software module 200 executed by the control system 140 can be configured to determine the time duration for the release phase by a module that randomly selects a duration time from a bracketed set of times that are empirically determined to provide a safe and effective release phase between occlusions phases (e.g., between about 2 second and about 15 seconds, between about 2 seconds and 6 seconds, and preferably between about 3 seconds and about 6 seconds). In an alternative embodiment, the operation 288 can be accomplished by the control system 140 implementing a duration time for the release phase in accordance with a predetermined pattern of release phase time periods. In yet another alternative embodiment, the operation 288 can be accomplished by the control system 140 calculating a time for ending the release phase based upon the data from the sensor signal input occurring during the release phase. As previously described, the control system 140 can be configured to detect and store the local maxima (or minima) of the sensor input signals occurring over a series of heartbeats during the release phase, calculate a curve fit function based upon the local maxima (or minima) data points, and thereafter calculate a duration time for the release phase based at least in part upon the curve fit function calculated from the local maxima (or minima) data points detected during the release phase.

Finally, after duration time for the release phase is reached, a new occlusion phase is started in operation 290. This cyclical process (e.g., operations 264 through 290) can continue for an extended period of minutes, thereby resulting in numerous cycles of occlusion phases and release phases. Accordingly, in some embodiments, the coronary sinus occlusion catheter 120 (FIGS. 1-2) may continue to intermittently occlude the coronary sinus (FIGS. 1-2) to thereby redistribute the venous blood flow to the damaged portion of the heart muscle tissue 30. The duration of time for using the coronary sinus occlusion catheter 120 to intermittently occlude the coronary sinus 20 may be determined by a practitioner based upon a number of factors, including the trend of the input sensor signals (e.g., the trend of coronary sinus pressure measurements as displayed on the user interface 142 of FIG. 7 or a derivate thereof), a measurement of particular bio-markers present in the patient's blood (e.g., lactate (which increases in the event of ischemia), potassium (an indicator of ischemic tissue), and the like), or a combination thereof or another input signal.

A number of embodiments of the invention have been described. Nevertheless, it will be understood that various modifications may be made without departing from the scope of the invention. Accordingly, other embodiments are within the scope of the following claims.

What is claimed is:

1. A system for treating a heart, the system comprising:

a coronary occlusion catheter including a heart vessel occlusion balloon to occlude venous blood flow from a heart vessel into a right atrium;

an external control console connectable with the coronary occlusion catheter to selectively inflate the heart vessel occlusion balloon for occluding the heart vessel during an occlusion phase and to deflate the heart vessel occlusion balloon for substantially non-occluding the heart vessel during a release phase, wherein the external control console includes: a controller configured to control the occlusion phase and the release phase, at least one sensor signal input to receive a hemodynamic sensor data signal from the coronary occlusion catheter, and a graphical user interface configured to simultaneously display a blood pressure numeric value, a heart rate numeric value, an occlusion phase time period, and a release phase time period, wherein the controller is configured to randomly select a duration time for the release phase from a predefined bracketed range of about 2 seconds and about 15 seconds, and wherein the controller is configured to automatically deflate the heart vessel occlusion balloon in response to detecting a hemodynamic sensor signal above a threshold value.

2. The system of claim 1, wherein the external control console is configured to couple with a proximal portion of the coronary occlusion catheter, and the at least one sensor signal input of the external control console includes at least a pressure sensor signal input indicative of a blood pressure the heart vessel occlusion balloon.

3. The system of claim 2, wherein the pressure sensor signal input is indicative of a coronary sinus pressure, and the external control console comprises a control circuit configured to activate a pneumatic subsystem to inflate the heart vessel occlusion balloon of the coronary occlusion catheter for a selected period of time based at least in part on the pressure sensor signal input indicative of the coronary sinus pressure.

4. The system of claim 3, wherein the external control console is configured to detect and store a series of local maxima or minima of the pressure sensor signal input during the occlusion phase, generate a curve fit function representing an envelope curve for said series of local maxima or minima, and determine a calculated release time for the occlusion phase based upon a time derivative of the curve fit function.

5. The system of claim 1, wherein the duration time for the release phase from the predetermined bracketed range comprises a time value from a predefined pattern of release phase duration times in the range about 2 seconds to about 6 seconds.

6. The system of claim 1, wherein the external control console is configured to end the occlusion phase after a controlled occlusion phase time period that occurs over a series of heartbeats.

7. The system of claim 1, wherein the sensor signal input of the external control console is configured to receive the hemodynamic sensor data signal during the occlusion phase, and the external control console further comprises a control circuit that activates a pneumatic subsystem to inflate the heart vessel occlusion balloon of the coronary occlusion catheter for a selected period of time based at least in part on the hemodynamic sensor data signal.

8. The system of claim 1, wherein the heart vessel occlusion balloon comprises a distal conical balloon portion, a central cylindrical balloon portion, and a proximal conical balloon portion, and wherein the coronary occlusion catheter comprises a plurality of lumens extending to a distal portion of the coronary occlusion catheter that carries the heart vessel occlusion balloon, wherein the external control console is configured to selectively inflate the heart vessel occlusion balloon for a controlled duration to intermittently occlude venous blood flow from the heart vessel into the right atrium during the occlusion phase time period, and wherein the external control console comprises a display device configured to simultaneously display, during the occlusion phase time period, at least a graph of pressure measurements over time, the blood pressure numeric value, a heart rate numerical value, the occlusion phase time period, and the release phase time period.

9. The system of claim 1, wherein the hemodynamic sensor data signal communicated to the external control console is indicative of a hemodynamic performance parameter selected from the group consisting of: coronary sinus pressure, fluid temperature in a coronary sinus, blood volume or mass flow rate in the coronary sinus, rate of change of the blood volume or the mass flow rate in the coronary sinus, acceleration of a vessel wall of the coronary sinus, displacement of a coronary sinus vessel, intra coronary sinus ECG, and contractility of the heart.

10. The system of claim 1, wherein the external control console is configured to detect and store a series of local maxima or minima of the hemodynamic sensor data signal during the occlusion phase.

11. The system of claim 10, wherein the external control console is configured to execute a curve fit function representing an envelope curve for the series of local maxima or minima, and wherein the external control console is configured to determine a calculated release time for the occlusion phase based upon a time derivative of the curve fit function.

12. The system of claim 11, wherein the external control console is configured to determine a weighted average time value that represents a point in time after a start of the occlusion phase and that is based upon the calculated release time and at least one previous release time value for at least one previous occlusion phase.

13. The system of claim 12, wherein the heart vessel occlusion balloon is a coronary sinus occlusion balloon sized to occlude venous blood flow from a coronary sinus into the right atrium.

14. The system of claim 1, wherein the external control console houses: a pneumatic subsystem for delivery of an inflation fluid to the heart vessel occlusion balloon, and control circuitry that receives the hemodynamic sensor data signal and that triggers the pneumatic subsystem to deflate the heart vessel occlusion balloon in response to detecting the blood pressure measurement above the threshold value.

15. The system of claim 14, wherein when the coronary occlusion catheter is connected to the external control console, the pneumatic subsystem of the external control console is in fluid communication with a balloon inflation lumen of the coronary occlusion catheter and the sensor signal input of the external control console is connected to a sensor line extending within the coronary occlusion catheter.

16. The system of claim 1, wherein the graphic user interface of the external control console is configured to configured to simultaneously display at least a graph of arterial pressure as a function of time, the blood pressure numeric value, the heart rate numeric value, the occlusion phase time period, and the release phase time period.

17. The system of claim 1, wherein the graphic user interface of the external control console is configured to display an alert in response to detecting the blood pressure measurement above the threshold value.

18. The system of claim 1, wherein the external control console is configured to end the occlusion phase after a predefined occlusion phase time period according to a predetermined pattern of occlusion duration times and release duration times.

19. The system of claim 1, wherein the external control console is configured to end the occlusion phase after a time period that occurs over a series of heartbeats.

* * * * *